(12) United States Patent
Baldwin et al.

(10) Patent No.: US 8,025,849 B2
(45) Date of Patent: Sep. 27, 2011

(54) ORAL FLUID COLLECTION, TRANSFER AND TRANSPORTATION DEVICE AND METHOD

(75) Inventors: Dene Baldwin, Oxford (GB); Ahmed Jehanli, Surrey (GB); Christopher William Hand, Oxfordshire (GB)

(73) Assignee: Cozart Bioscience, Abingdon, Oxfordshire (GB)

( * ) Notice: Subject to any disclaimer, the term of this patent is extended or adjusted under 35 U.S.C. 154(b) by 2218 days.

(21) Appl. No.: 10/636,888

(22) Filed: Aug. 7, 2003

(65) Prior Publication Data
US 2004/0082878 A1 Apr. 29, 2004

(30) Foreign Application Priority Data

Aug. 14, 2002 (GB) .................................. 0218918.1

(51) Int. Cl.
*G01N 21/75* (2006.01)
*G01N 31/22* (2006.01)
*G01N 33/52* (2006.01)
(52) U.S. Cl. ........ 422/401; 422/400; 422/406; 422/408; 422/417; 422/418; 422/420; 422/430
(58) Field of Classification Search .................. None
See application file for complete search history.

(56) References Cited

U.S. PATENT DOCUMENTS

| | | | | |
|---|---|---|---|---|
| 4,014,322 A | * | 3/1977 | Shah | 600/573 |
| 4,580,577 A | | 4/1986 | O'Brien et al. | |
| 4,846,583 A | * | 7/1989 | Yamamoto | 374/163 |
| 5,268,148 A | * | 12/1993 | Seymour | 422/101 |
| 5,335,673 A | | 8/1994 | Goldstein et al. | |
| 5,479,937 A | * | 1/1996 | Thieme et al. | 600/573 |
| 5,830,410 A | | 11/1998 | Thieme et al. | |
| 6,303,081 B1 | | 10/2001 | Mink et al. | |
| 6,365,417 B1 | * | 4/2002 | Fleming et al. | 436/514 |
| 6,372,516 B1 | * | 4/2002 | Sun | 436/518 |
| 6,489,172 B1 | * | 12/2002 | Bachand et al. | 436/180 |
| 2001/0034068 A1 | | 10/2001 | Spivey et al. | |
| 2002/0015663 A1 | | 2/2002 | Goldstein et al. | |
| 2003/0064526 A1 | * | 4/2003 | Niedbala et al. | 436/165 |

FOREIGN PATENT DOCUMENTS

| | | |
|---|---|---|
| EP | 0 734 686 | 10/1996 |
| WO | WO 0004381 A1 | 1/2000 |
| WO | WO 0149821 A1 | 7/2001 |
| WO | WO 03/028889 A1 | 4/2003 |

* cited by examiner

*Primary Examiner* — Jill Warden
*Assistant Examiner* — Neil Turk
(74) *Attorney, Agent, or Firm* — Flynn, Thiel, Boutell & Tanis, P.C.

(57) ABSTRACT

An oral fluid collection and transfer device comprises a collection device (10) and a test cartridge (100). The collection device includes a frame or chassis (14), and an absorbing pad (12) for absorbing oral fluid and which is secured around part of the frame with part of the frame protruding from the pad. A collapsible cover (16) covers the absorbing means and has apertures (68) for the ingress of oral fluid into contact with the absorbing pad. A cap (18) covers the part of the frame protruding from the absorbing pad. The cap and the cover latch together to surround the frame and the absorbing pad. The device also includes a fluid adequacy indicator (20) in the form of an electrical circuit with an LED (66) which is completed when the absorbing means has absorbed a predetermined volume of oral fluid.

23 Claims, 17 Drawing Sheets

ORAL FLUID COLLECTION, TRANSFER AND TRANSPORTATION DEVICE AND METHOD

BACKGROUND OF THE INVENTION

This invention relates to apparatus for the collection and assay of analytes in oral or other fluids. The invention relates further to a method for the controlled transfer of oral fluid from a collection device to a test cartridge, and to apparatus including a transportation vial for the secure transportation of a sample of oral fluid to a laboratory for test verification.

Bodily fluids such as blood, urine or oral fluid have traditionally been used for the purpose of testing for the presence of particular analytes such as drugs, hormones, pollutants, viral and bacterial antigens in the body. Oral fluid is the term used to describe all of the fluids that can be found in the mouth cavity. It is commonly referred to as saliva but is in fact composed of a number of other components such as bacteria, food debris, enzymes, water, salts and mucoprotein in addition to saliva. The use of oral fluid for analyte testing has a number distinct advantages over other biological fluids. It is a painless, non-invasive technique and the collection is straightforward, can be performed by the donor, and is easily observed. Oral fluid is becoming increasingly used as a sample matrix for testing of substances such as drugs of abuse, infectious diseases and for DNA testing.

For many organisations, drug testing is an important and necessary duty. Police officers for example may wish to conduct roadside tests to determine whether a motorist has taken an illegal substance that will affect his driving capabilities. The criminal justice system often conducts random drug tests on prison inmates, detainees or individuals on probation in order to monitor the presence of illegal drugs. Similarly, sporting authorities may wish to conduct random tests on athletes to detect the presence of performance-enhancing drugs. These and other applications may require testing for the presence of drugs such as cannabinoids, amphetamine, cocaine, opiates, benzodiazepines, methadone, methamphetamine and phencyclidine amongst others.

A number of prior systems for the collection of oral fluid have been developed, most of which rely on a collection device made from an absorbent material which is placed in the mouth. One prior system for example uses a rayon ball which is placed in the mouth for a certain period of time. The ball is subsequently placed into a syringe mechanism to extract the absorbed oral fluid prior to testing. This system suffers from the disadvantage that it is difficult to know when an adequately-sized sample has been obtained, and a subjective judgement is required by the operator to decide when a sufficient volume of fluid has been collected. This results in considerable variation in volume of oral fluid collected and may affect the consistency and reliability of testing. For example, if an insufficient (and undefined) volume of oral fluid is used for testing, then the quantity of any compound present in the sample may be too small to detect.

Another system draws oral fluid from the mouth by osmotic pressure into a small plastic sack consisting of a semi-permeable membrane containing high molecular weight sugars. This system suffers the disadvantage that it may take between 10 to 15 minutes to collect a sufficient volume of oral fluid. This problem is compounded in the case of drug addicts who often suffer from dry mouths and for whom collection of an adequate volume of oral fluid make take an inordinate length of time.

A further system uses an aspirator to draw and de-bubble oral fluid directly from the mouth into a test cartridge housed in an instrument casing. This system suffers the drawback that it is large, cumbersome and lacks portability.

Our International Patent Application WO00/04381 (and US Patent Application 2001/0034068 based thereon) describes a system which uses an absorbent foam pad on an indicator handle which turns blue to signal that a sufficient volume of oral fluid has been collected. The collection pad is inserted into a tube having a separator filter to extract oral fluid from the pad which is then transferred to a test cartridge by carefully pipetting a number of drops onto the cartridge. The ease in maintaining reliability of testing using this system may however be significantly reduced if collection takes place in a turbulent environment, for example by the roadside.

Further examples of prior systems are described in the following patent applications. The device described in international patent application WO 01/49820 comprises an absorbent foam swab having a tether which is placed into a port of a testing device The tether may be used to pull and compress the foam swab thereby transferring a volume of fluid from the swab to a test strip or a sample container. U.S. Pat. No. 4,580,577 describes a device having an absorbent mass which is placed in a chamber and compressed by a piston screwed down into the chamber. Fluid is thereby transferred from the absorbent mass to a collection vial. European Patent Application 0 734 686 describes an oral fluid sample collection device comprising an absorbent cotton pad on a plastic handle with a colour dye sample adequacy indicator. U.S. Pat. No. 6,303,081 describes a collection device incorporating a bite plate in which oral fluid is drawn by capillary action from the mouth, through a wick to a chromatography strip. United States Patent Application 2002/0015663 describes a syringe mechanism to transfer oral fluid from the mouth to a test strip. Another collection system is described in U.S. Pat. No. 5,335,673.

In view of the disadvantages of prior systems, we have appreciated the need for a non-invasive system for the collection and testing of oral fluid which is portable, quick and easy to use. We have further appreciated the need to eliminate subjective judgement and reduce errors on the part of the operator to enable the system to produce reliable, reproducible and consistent results. Furthermore, we have appreciated the need to allow point-of-care (on-site) collection and testing with the option of sending the collected specimen to a laboratory for further testing or the option of sending the collected sample directly to a laboratory without an on-site analysis.

SUMMARY OF THE INVENTION

The invention in its various aspects is defined in the independent claims below to which reference may now be made. Advantageous features of the invention are set forth in the appendant claims.

In one aspect of the present invention, a collection device is provided to allow the collection of a predetermined volume of oral fluid from the mouth. A test cartridge is provided for on-site testing of oral fluid to detect the presence of particular compounds such as drugs. A transportation vial may also be provided for the secure transportation of a sample of oral fluid to a laboratory for test verification. The system facilitates the transfer of a predetermined volume of oral fluid from the collection device to the test cartridge and the transportation vial with the minimum of errors. The same system can be applied for the collection of other fluids—both biological and non-biological (eg water, beer and other drinks)—and to the analysis of compounds other than drugs.

A preferred system embodying the invention is described in more detail below with reference to the drawings.

The collection device of this embodiment comprises a means to absorb oral fluid. This can be an absorbent medium in the form of a pad made from a foam or cellulose material. The collection device further comprises a fluid adequacy indicator to signal to the operator (who may or may not be the oral fluid donor) when a sufficient volume of oral fluid has been collected. The fluid adequacy indicator or detector may consist of a fluid detection circuit comprising a power source such as a battery, a fluid sensitive contact and an alert device such as a buzzer or LED (light emitting diode). In this embodiment, the fluid sensitive contact is bridged when a sufficient volume of oral fluid has been absorbed by the absorbent pad. The circuit is thus completed and the power source activates the alert means thereby providing the operator with a signal as to when a sufficient volume of oral fluid has been collected.

In another embodiment, the fluid detection circuit can further comprise a timing device and multiple sensors to improve the accuracy and control of fluid collection. The timing device can allow a small additional time after the fluid adequacy detector senses that an adequate amount of fluid is present. In yet a further embodiment, the power source and alert means are housed in a separate unitary device in the form of a wand which is temporarily connected to the collection device via an electrical socket during operation. This configuration facilitates the use of rechargeable batteries and reduces the waste of components in disposable parts of the system. In another embodiment, a chemical based fluid adequacy indicator is used. In this embodiment, the absorbent pad contains a Porex®, glass fibre or cellulose wick. As oral fluid travels up the wick, a fluid sensitive chemical dye is re-hydrated causing a change in colour of the dye which is displayed to the operator through a window in the collection device. Alternatively, a coloured dye travels with the oral fluid until visible in a window.

In the preferred embodiment of the invention, the absorbent pad is housed within a collapsible tube or cover to prevent seepage of oral fluid from the absorbent pad during collection. The collapsible tube also provides rigidity to facilitate the insertion into the test cartridge and compression of the absorbent pad. The donor is also able to chew the end of the collapsible tube, resulting in a strong physiological response of saliva gland stimulation. The rate of oral fluid production is thus increased and the collection time is reduced. In another embodiment, stimulation of the saliva glands is activated by a physiological response to a flavouring or odour incorporated into the collection device.

Following the collection of oral fluid, the collection device can be inserted into a test cartridge whereupon the absorbent medium that is the absorbent pad undergoes a controlled degree of compression, which action transfers a predetermined volume of oral fluid from the collection device to the test cartridge. The controlled degree of compression is achieved by pushing the collection device into a collection chamber contained in the test cartridge. In the preferred embodiment, the absorbent pad rests at the lower end of the collapsible tube and is compressed by a plunger or compression structure formed from a chassis contained in the collection device. In an alternative embodiment, the absorbent pad is attached to one end of the chassis and is the same length as the collapsible tube so that the collapsible tube cannot be compressed without also compressing the absorbent pad. In this embodiment, the depth of the collection chamber is shorter than the uncompressed length of the collapsible tube and absorbent pad so that the collapsible tube and absorbent pad cannot be fully inserted into the collection chamber without being at least partially compressed. The absorbent pad and collapsible tube are compressed, squeezing out a predetermined volume of the absorbed oral fluid. The compression is controlled by restricting the amount by which the absorbent pad can be compressed. This controlled degree of compression provides a quick, easy and error free means for transferring a precise volume of oral fluid to the test cartridge, enabling consistent and accurate testing. The combination of the collection of a predetermined volume of oral fluid, followed by the controlled degree of compression of the absorbent pad, results in a known volume of oral fluid being applied to the test cartridge.

In one embodiment, the collection device comprises a releasable locking mechanism to temporarily fix the collection device inside the test cartridge in relative positions such that the locking mechanism is activated only when the absorbent pad is compressed by a predetermined amount, thereby providing a controlled degree of compression. The oral fluid transferred from the collection device to the test cartridge is conveyed to a test strip which is subsequently analysed by a compatible analysis device or visually by the operator. In one embodiment the oral fluid is transferred to multiple strips simultaneously thereby allowing a plurality of compounds to be assayed for in a single device. In another embodiment, the test cartridge comprises a series of markings which identifies a test cartridge as appropriate for the testing of a particular compound. The analysis device reads these markings and alters its analysis accordingly.

After initial testing, the collection device is inserted into a transportation vial wherein at least a proportion of the remaining oral fluid contained within the collection device is transferred to a sample vial which may contain a preservative substance to prevent degradation of the sample during transportation. The collection device and transportation vial are repackaged and sealed with a tamper proof seal before being returned to a laboratory for confirmation tests.

BRIEF DESCRIPTION OF-THE DRAWINGS

The preferred embodiment of the invention will now be described in more detail, by way of example, with reference to the drawings in which.

DETAILED DESCRIPTION OF THE PREFERRED EMBODIMENT

Figure 1:
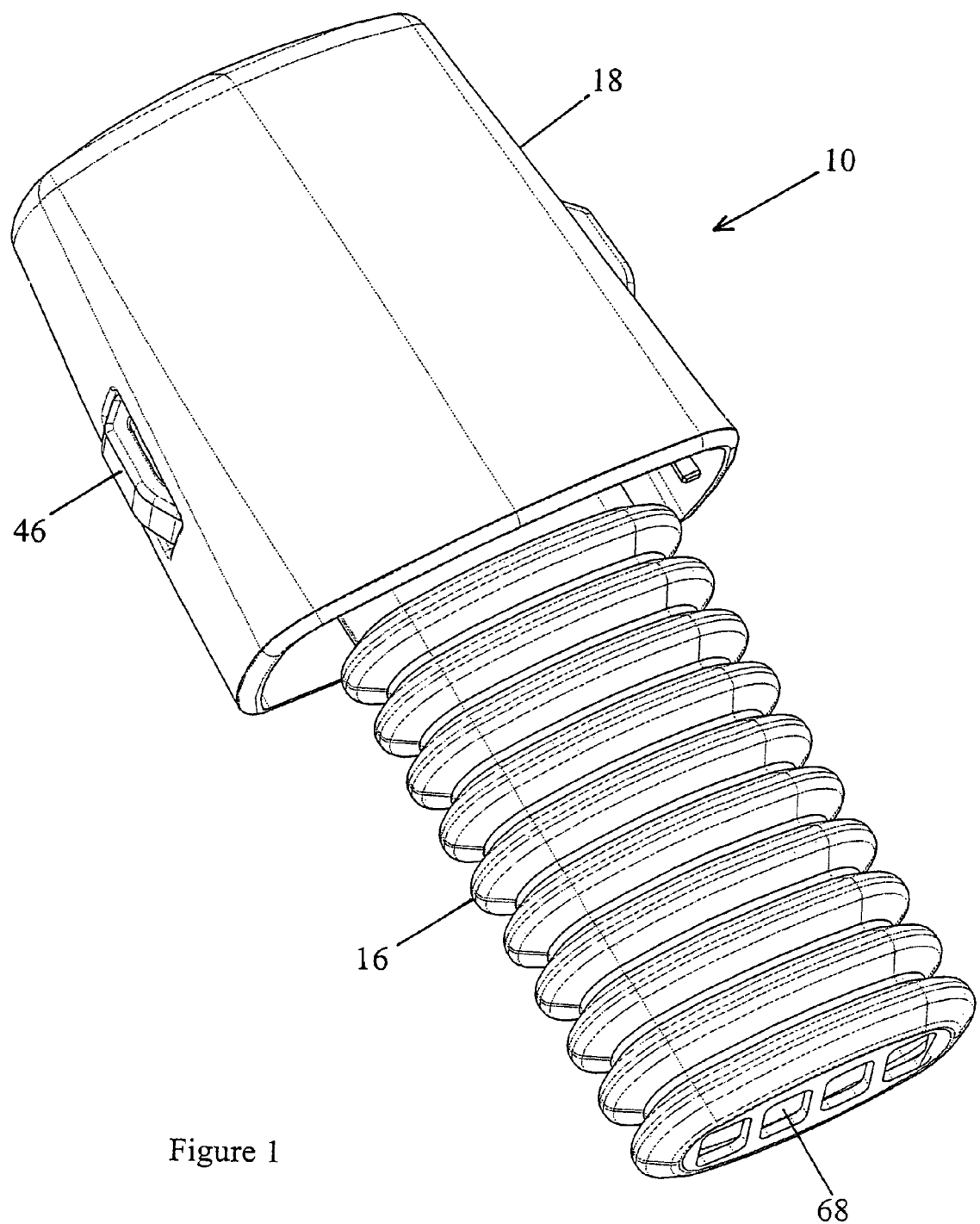
FIG. 1 shows an assembled oral fluid collection device.
Figure 2:
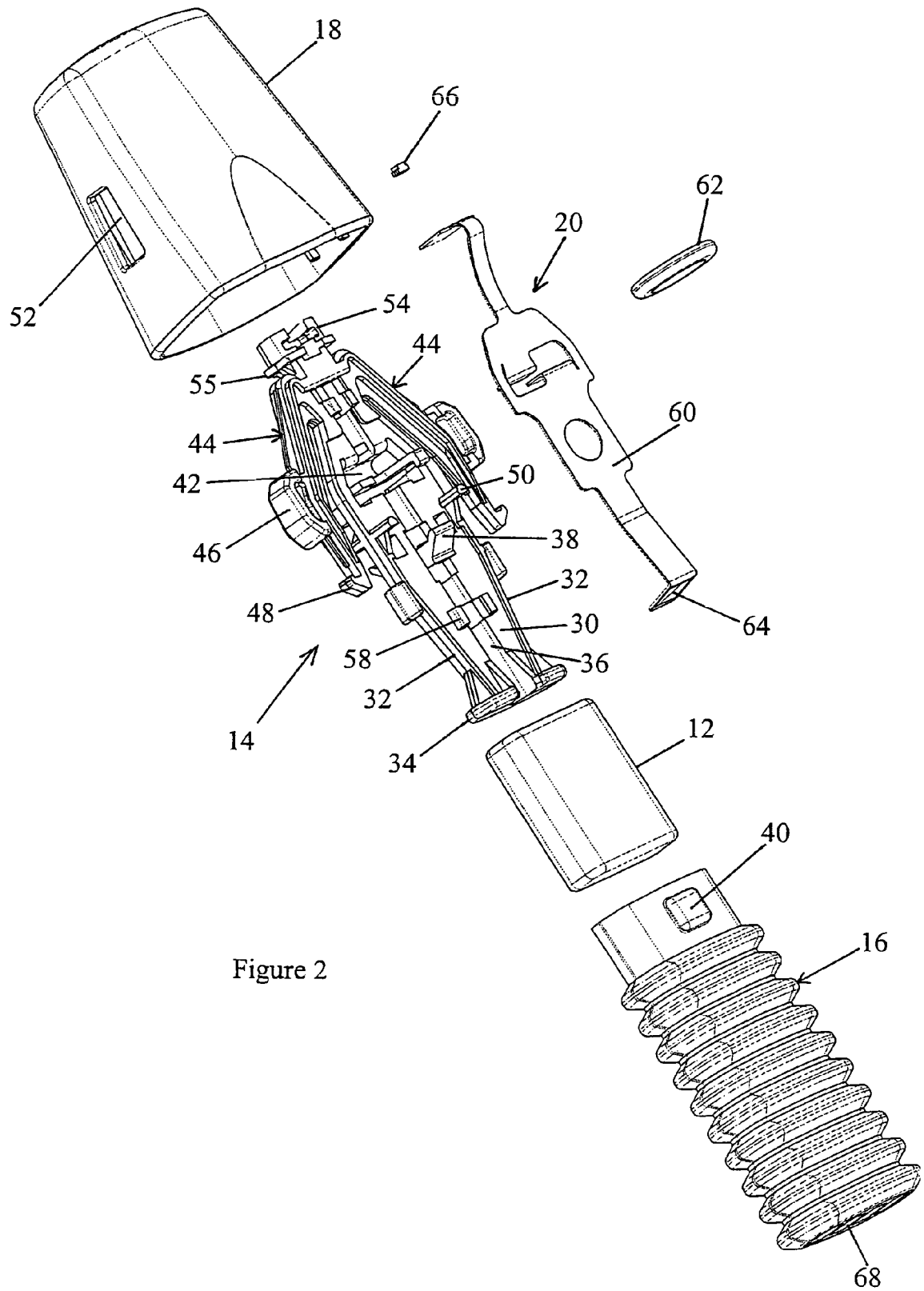
FIG. 2 is an exploded view of the oral fluid collection device of FIG. 1.

FIG. 1 shows an assembled collection device 10 provided to collect a sample of fluid from the oral cavity. FIG. 2 is an exploded view of the collection device 10 of FIG. 1 showing its component parts. The collection device 10, which is preferably disposable, comprises a compressible absorbent pad 12 to absorb fluid from the oral cavity, which expands to hold the fluid within its matrix. In the preferred embodiment, the absorbent pad 12 is generally oblong in shape and made from an absorbent foam such as medical grade foam, or cellulose material. It is understood however, that the absorbent pad 12 could be made from other materials and is not restricted to being of a particular form or proportion. The absorbent pad 12 is sufficiently large and absorbent to retain a volume of oral fluid adequate for reliable testing. An adequate volume of oral fluid is considered for the present purpose to be at least 0.6 ml. The fluid capacity of the absorbent pad 12 can be increased or decreased if necessary by respectively increasing or decreasing the dimensions and absorbency of the absorbent pad 12. The absorbent pad 12 may contain a wick to facilitate the migration of oral fluid through its structure.

The other main components of the collection device are a frame or chassis 14, a collapsible cover in the form of a tube 16, a protective cap 18, and a fluid adequacy indicator 20. The chassis 14, collapsible tube 16, and cap 18 are made of plastics materials. The fluid adequacy indicator 20 is made as described in more detail below.

Figure 5:
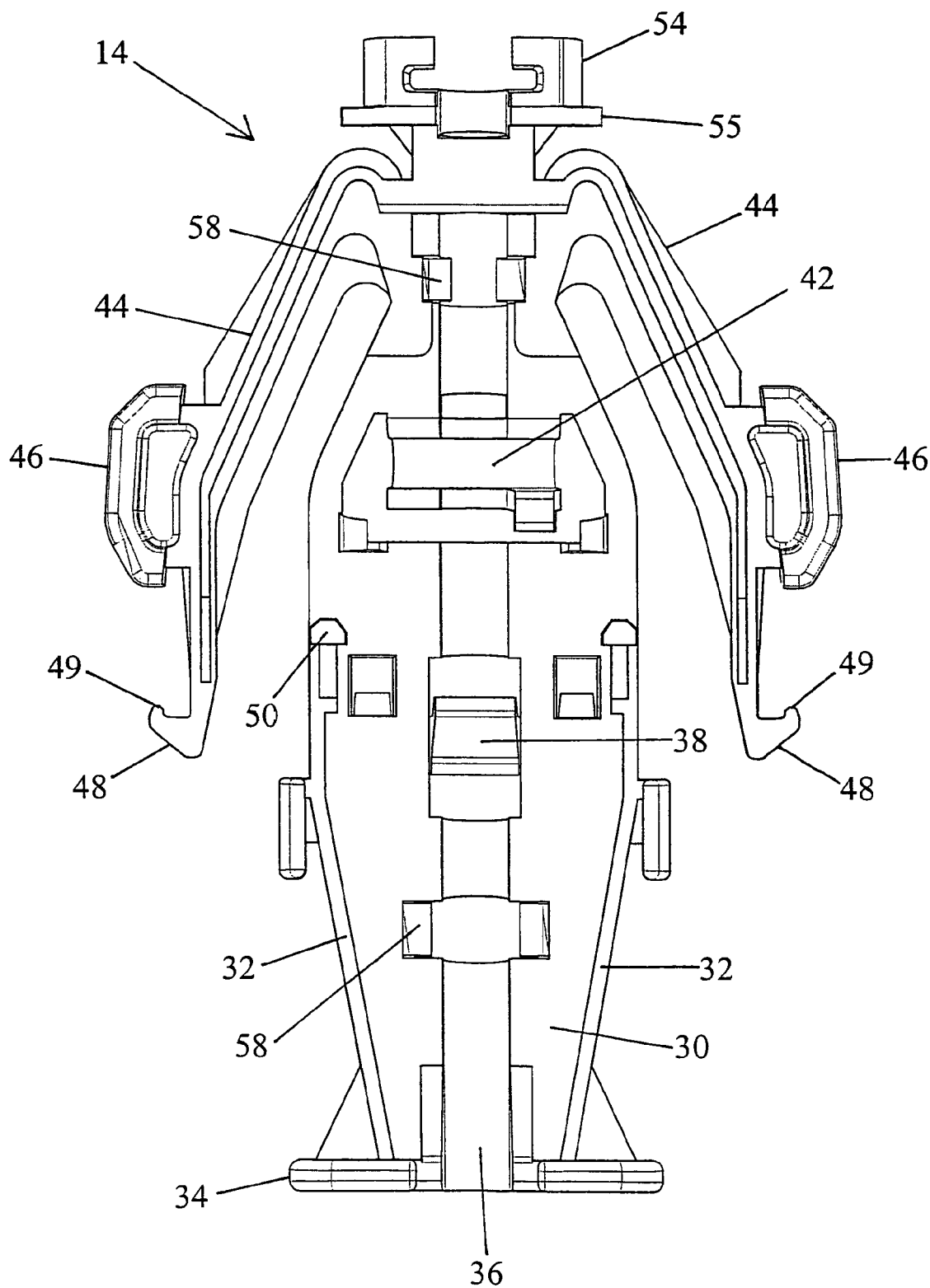
FIG. 5 is a front view of the chassis used in the fluid collection device of FIG. 1.

The generally planar chassis 14 is made by injection moulding and is shown in FIGS. 2, 3, 4 and 5. The chassis 14 is symmetrical about the vertical centre line in FIG. 5. The chassis 14 comprises a generally-rectangular plate section 30 which has upstanding ribs 32 at either side, an upstanding rib 34 at its lower end as seen in FIG. 5, and a central upstanding rib 36 along its vertical centre line. These ribs all extend both above and below the plate 30 and provide rigidity to the structure. The upstanding rib 34 at the lower end of the chassis 14 also forms the base of a plunger or compressor structure which acts to compress the absorbent pad 12, which process will be described in greater detail below. The central rib 36 on each side of the plate 30 carries an upstanding protrusion 38 which is designed to engage with a respective one of two apertures 40 on the top periphery of the collapsible tube 16 to fix the chassis 14 and the tube 16 together. The lower side of the protrusion 38 is chamfered to allow the tube 16 to pass over the protrusions 38 by outward deformation of the top side walls of the tube 16. Once the tube 16 is in position it is then retained by the protrusions 38. It can be released by inward pressure across the width of the top of the tube 16.

The absorbent pad 12 is shorter than the uncompressed length of the collapsible tube 16 and is located at the lower end of the collapsible tube 16 so that the lower surface of the absorbent pad 12 is located next to the openings 68 at the lower end of the collapsible tube 16. The chassis 14 passes through the open upper end of the collapsible tube 16 so that a first part of the chassis 14 is contained within the collapsible tube 16, and a second part of the chassis 14 protrudes from the upper end of the collapsible tube 16. The plunger structure 34 lies in the interior of the collapsible tube 16. The size and position of the plunger 34 is such that upon construction of the collection device 10, when the collapsible tube 16 is in an uncompressed state, the lower surface of the plunger 34 contacts the upper surface of the absorbent pad 12 without compressing the absorbent pad 12.

The plate 30 has a central rectangular aperture 42 which is sized to receive a small button-type battery 62. Appropriate mouldings are provided to retain the battery 62 in the aperture 42.

The upper end of the chassis 14 as seen in FIG. 5 carries a pair of oppositely-located flexible arms 44 which extend outwardly and downwardly around the respective sides of the plate 30 about half-way down the plate 30. Each arm 44 carries a button portion 46 and a latching portion 48 at the tip of the arm 44. The latching portions 48 are used when the collection device 10 is inserted in the test cartridge 100 of FIG. 5, as described below. Inward pressure on the button portions 46 causes inward movement of the latching portion 48, to allow separation of the collection device 10 and the test cartridge 100. The tips of the latching portions 48 comprise upstanding ridges 49 which prevent the latching portions 48 becoming freed from the locking holes 116 in the test cartridge 100 during the oral fluid transfer process.

Figure 10:
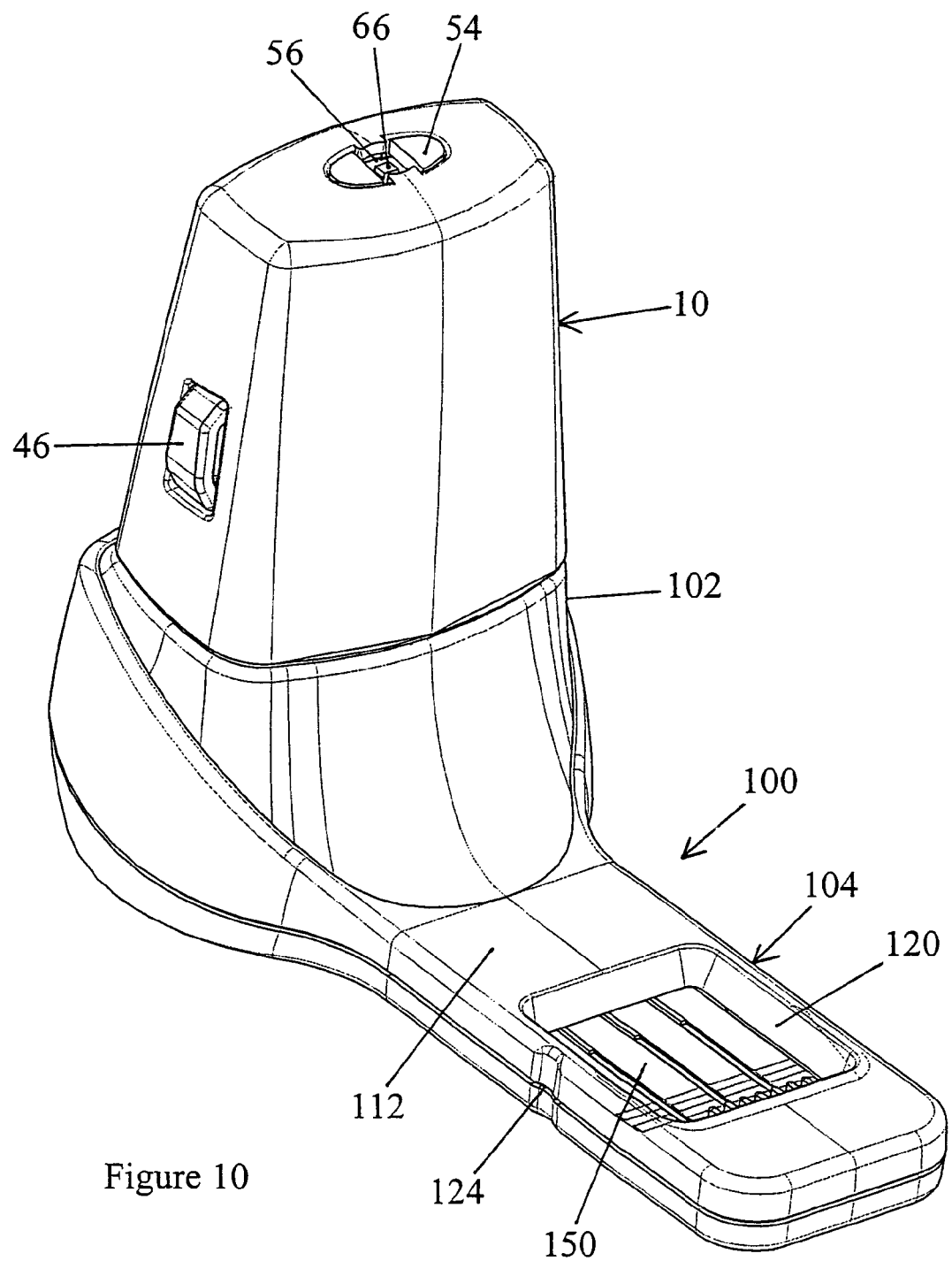
FIG. 10 is an isometric view of the collection device of FIG. 1 fully inserted into the test cartridge of FIG. 7.
Figure 11:
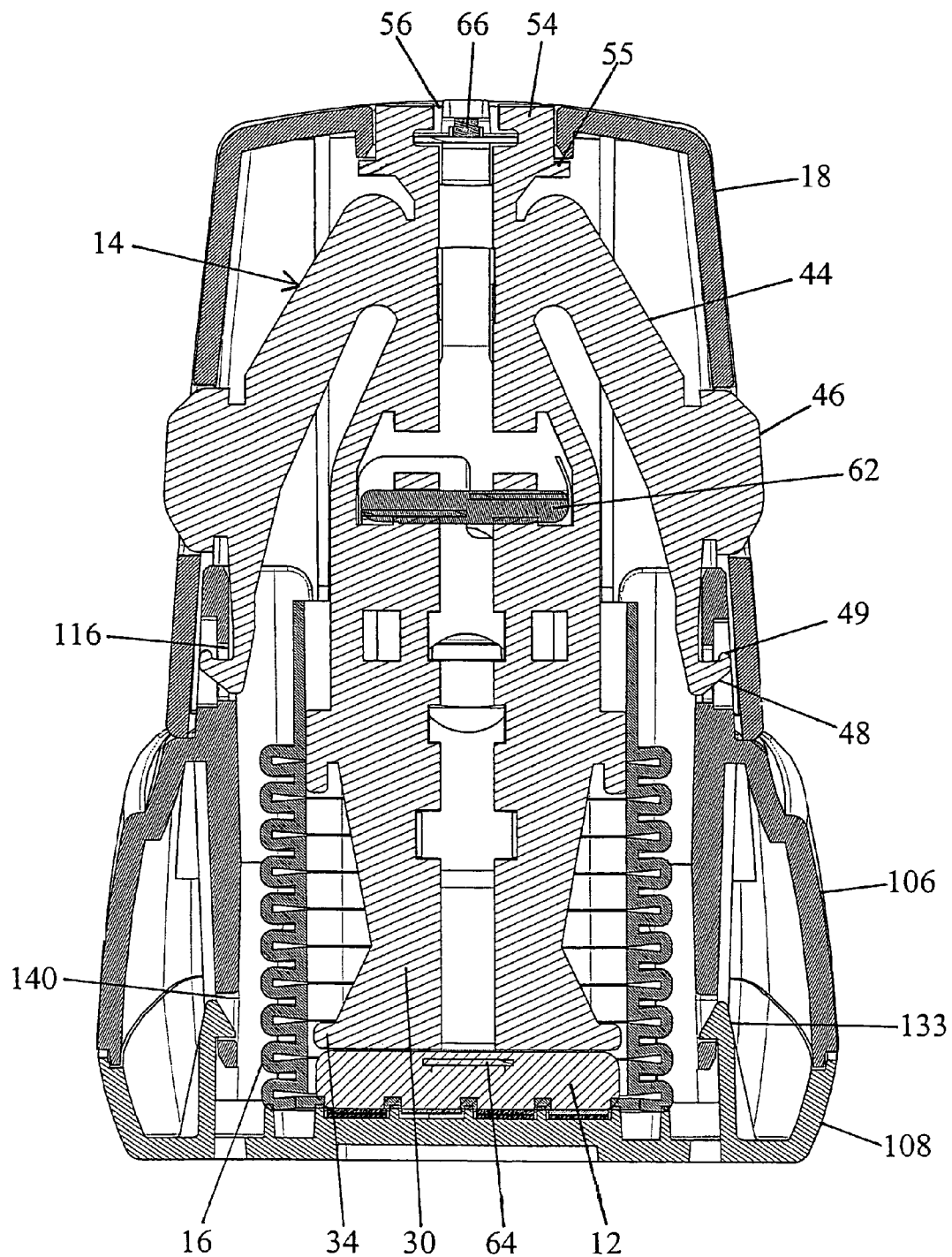
FIG. 11 is a front cross-section of the collection device fully inserted into the test cartridge, taken on the line IX-IX in FIG. 9.
Figure 12:
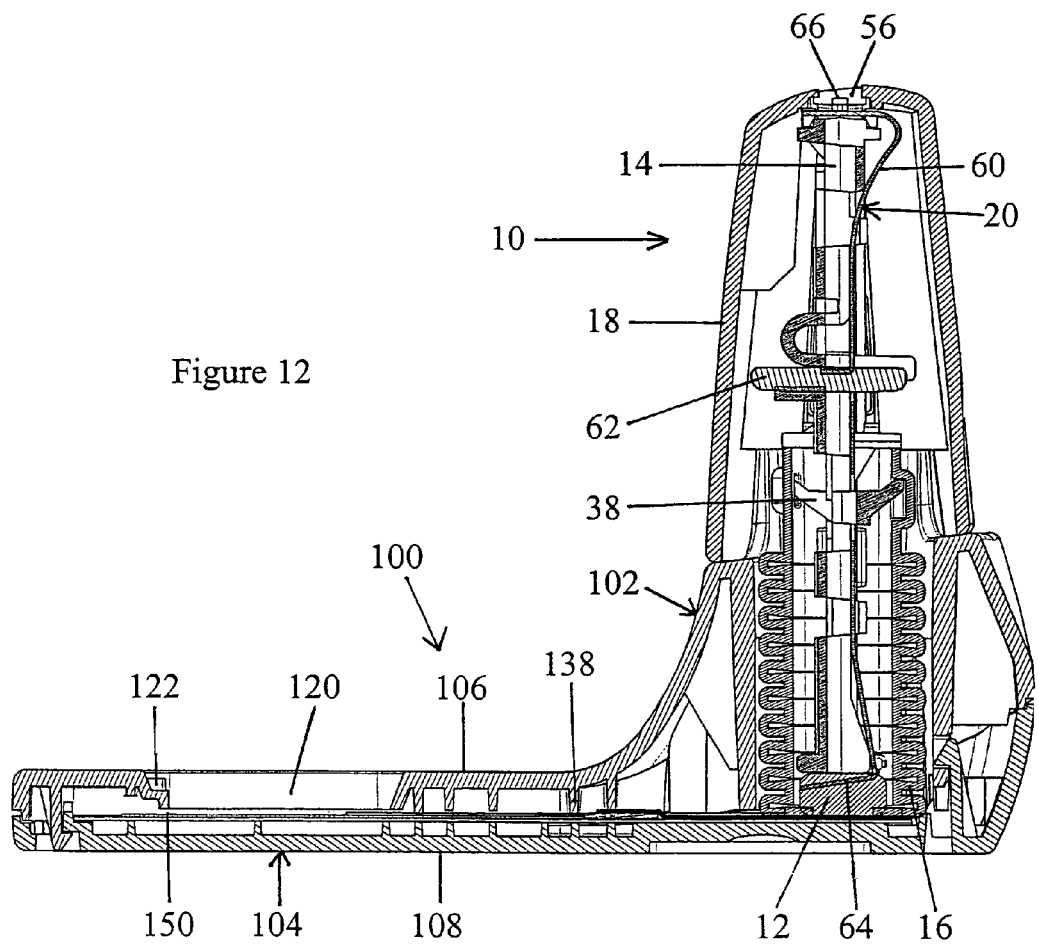
FIG. 12 is a side cross-section of the collection device fully inserted into the test cartridge, taken on the line X-X in FIG. 9.

The plate 30 carries upwardly and downwardly protruding spacers 50 to locate the chassis 14 centrally within the cap 18. When the chassis 14 is fully within the cap 18, the button portions 46 protrude through side apertures 52 in the cap 18 which help hold the chassis 14 into place inside the cap 18. The button portions 46 can thus be depressed inwardly by an operator to move the latching portions 48 inwardly. The spacers 50 engage the inside of the cap 18 to locate the chassis 14 in a fixed position within the cap 18. The top portion 54 of the chassis 14 as seen in FIG. 5 protrudes through an aperture 56 in the top of the cap 18, as indicated in FIGS. 10, 11 and 12. The base of the top portion 54 of the chassis 14 comprises a shelf or stopper 55 which has a larger area than the aperture 56 in the top of the cap 18 so that when the top portion 54 protrudes through the aperture 56, the stopper 55 engages the interior of the cap 18 and is prevented from passing through the aperture 56. When downwards pressure is applied to the cap 18 so that the tube 16 is compressed, the chassis 14 will tend to move upwards inside the cap 18. The stopper 55 prevents upward movement of the chassis 14 within the cap 18 and allows for greater control of the magnitude of the compression of the collapsible tube 16 and absorbent pad 12.

The purpose of the chassis 14 is three fold. First it acts as a frame to hold the various components of the collection device 10 together. Secondly it holds the fluid adequacy indicator 20 which signals when a sufficient volume of oral fluid has been absorbed by the absorbent pad 12. Thirdly it forms part of the releasable locking mechanism which acts to fix the collection device 10 into place when it is inserted into the test cartridge 100 which is described below.

Figure 6:
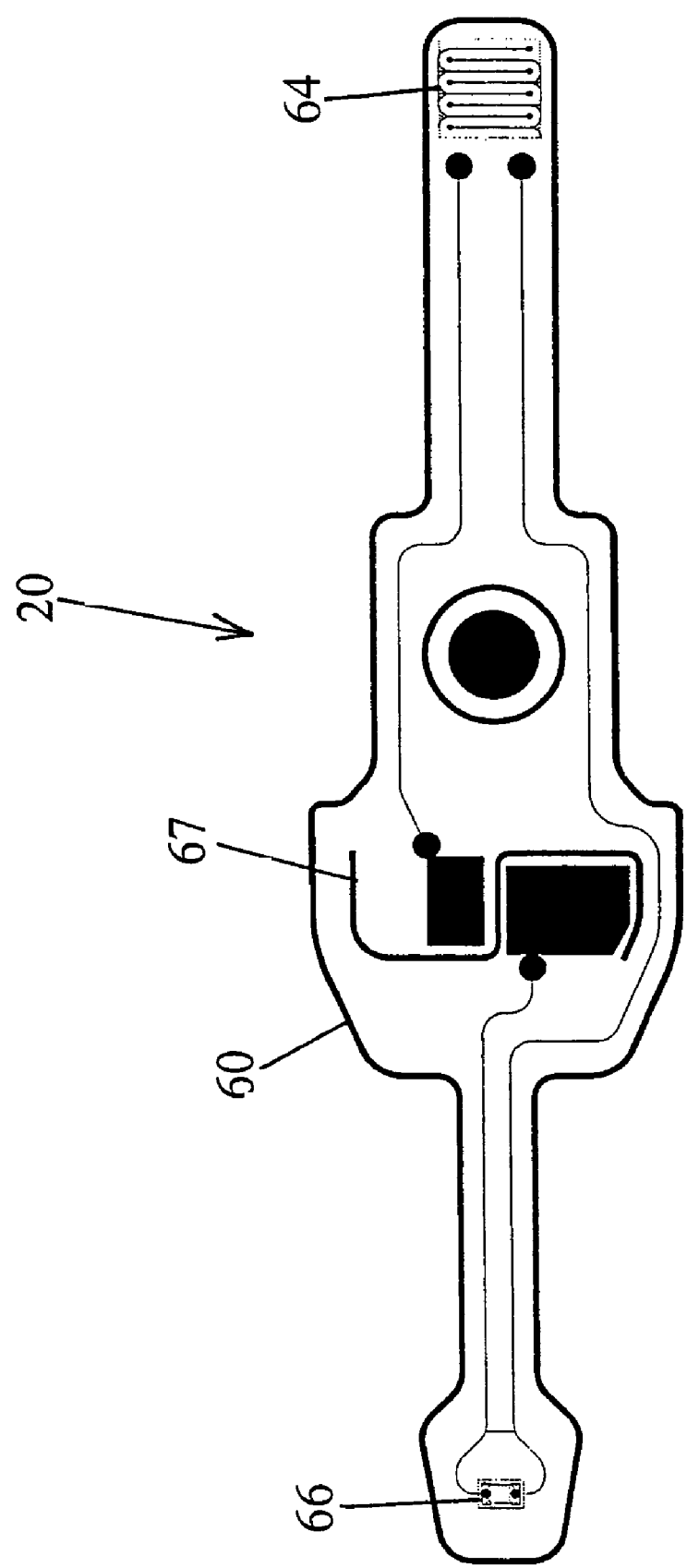
FIG. 6 is a track diagram of the fluid adequacy circuit.

The fluid adequacy indicator 20 comprises a fluid detection circuit, and is provided with a power source in the form of a battery 62, fluid sensitive contact 64 comprising two series of conducting elements, and an alert element such as an LED 66. FIG. 6 is a track diagram for the fluid adequacy circuit. The fluid detection circuit 20 is formed with silver ink on a thin layer of non-conducting material. In the preferred embodiment, the circuit is formed on a polyester strip 60 which is retained on the chassis 14 by means of clips 58 moulded as part of the chassis. Additionally, the head of the polyester strip 60 is tapered and is fixed within a slot in the top portion 54 of the chassis 14. The polyester strip 60 may be laid flat on the chassis 14 but this is not essential. The battery 62 is held in place on the chassis 14 by mouldings around the aperture 42. The battery 62 passes through an aperture in the polyester strip 60 which has two adjacent contact flaps 67 laying either side of the aperture, which are folded so they lie perpendicular to the strip 60. Each of the positive and negative power terminals of the circuit are contained on a respective one of the flaps 67 which contact with opposite sides of the battery 62. The fluid sensitive contact 64 is formed at the end of the polyester strip 60 which bears against the lower surface of the rib 34 at the bottom of the chassis 14. Upon assembly of the collection device 10, the rib 34 at the lower end of the chassis 14 rests against the upper surface of the absorbent pad 12, and thus the fluid sensitive contact 64 also rests against the absorbent pad 12. The fluid sensitive contact 64 is formed as a grill or grid structure with two inter-locking series of parallel conducting elements. The fluid sensitive contact 64 is laid out with small gaps between conducting elements so that the two series of elements are electrically insulated from each other. The conducting elements of one particular series are electrically connected. The circuit 20 is arranged so that power is supplied to the LED 66 from the battery 62 only when the fluid sensitive contact 64 is bridged. The fluid sensitive contact 64 is bridged when oral fluid fills the spaces in between the conducting elements so that current can flow from one series of conducting elements to the second series of conducting elements through the oral fluid. The fluid sensitive contact 64 is designed so that it is bridged only when a sufficient volume of oral fluid has been absorbed by the absorbent pad 12. The sensitivity of the fluid sensitive contact 64 can be increased or decreased by respectively decreasing or increasing the spacing between the conducting elements. The LED 66 is positioned to coincide with the opening 56 in the head of the protective cap 18 so as to be visible to the operator. It is understood that the LED 66 could be replaced by any component which provides the operator with a visual, audible, tactile, or other alert signal. The LED 66 could be replaced by, for example a buzzer. The fluid detection circuit 20 can be assembled by folding the polyester strip 60 holding the fluid detection circuit 20, inserting the battery 62 into the aperture in the polyester strip 60 so that the two flaps 67 bear against opposite sides of the battery 62 and attaching the polyester strip 60 onto the surface of the chassis 14.

Figure 3:
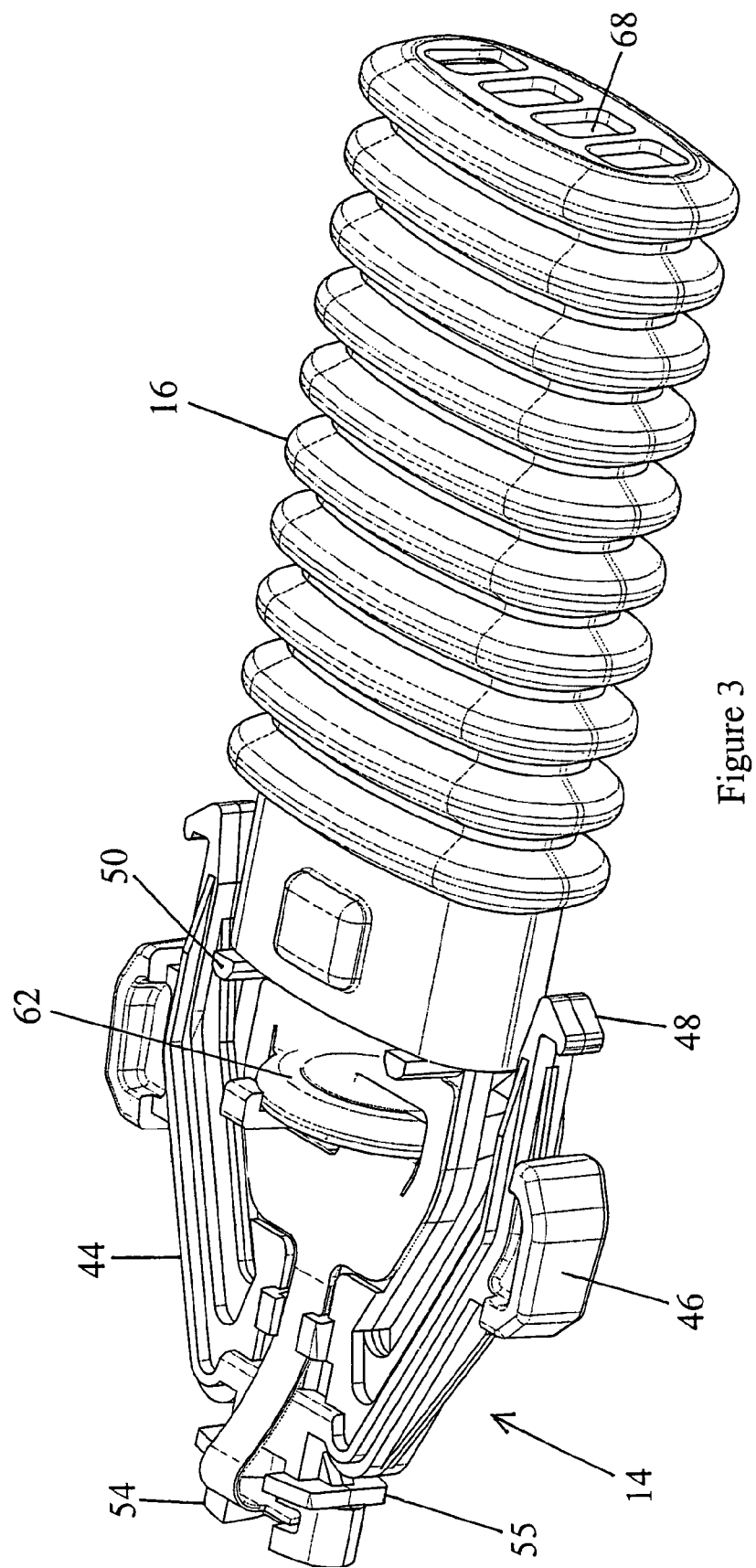
FIG. 3 shows a partially assembled collection device.
Figure 4:
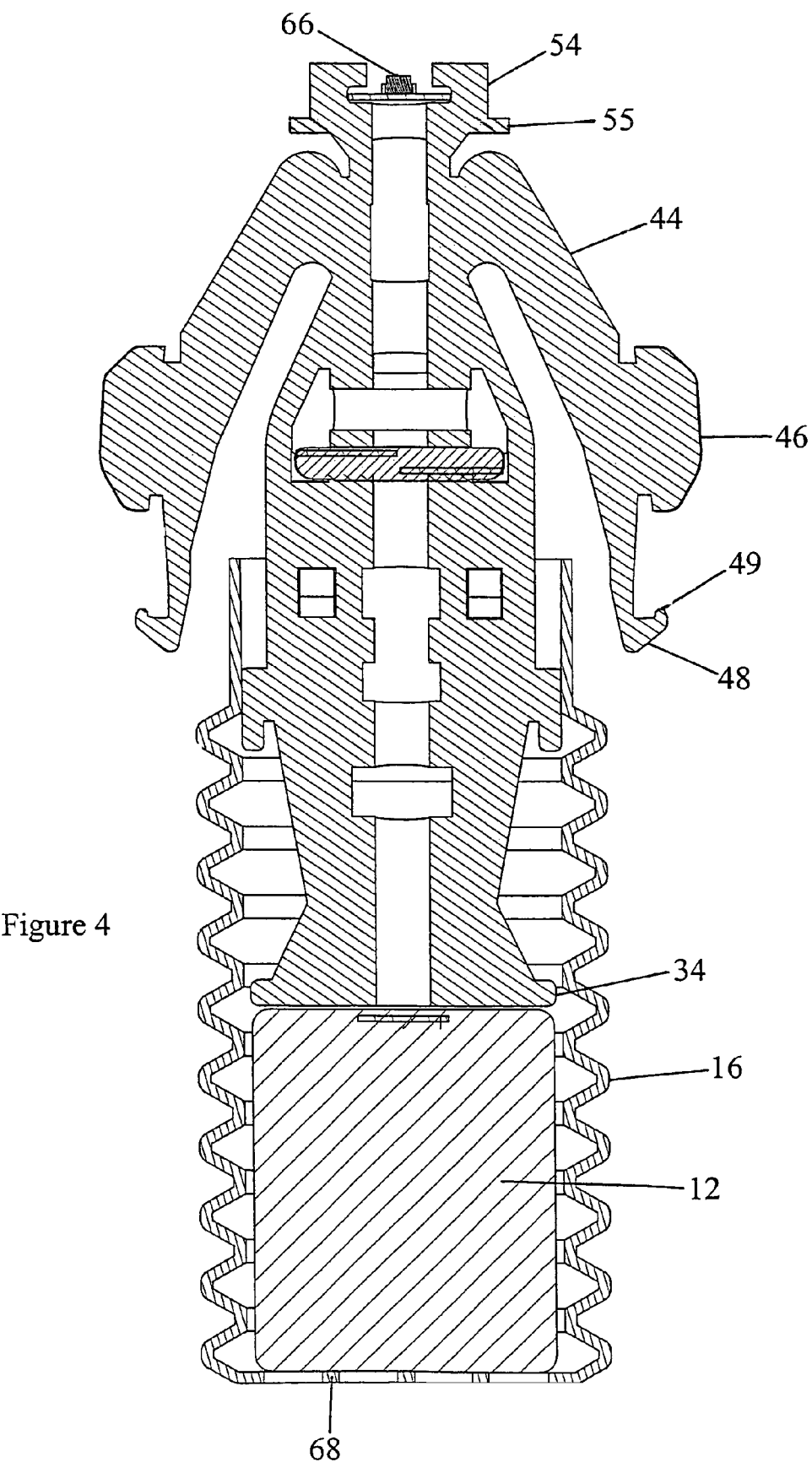
FIG. 4 is a front cross section of the partially assembled collection device of FIG. 3.

FIG. 3 shows a partially assembled collection device 10 comprising the chassis 14, fluid adequacy indicator 20, absorbent pad 12, and collapsible tube 16 before the cap 18 is attached.

The collapsible tube 16 is of ovular cross section, and is made from a durable, flexible and non-toxic material. The walls of the collapsible tube 16 are corrugated with the direction of the corrugations lying perpendicular or transverse to the length of the collapsible tube 16, allowing the collapsible tube 16 to be compressed in the lengthways direction. The collapsible tube 16 has openings 68 at its lower end, allowing oral fluid to enter the collapsible tube 16 and become absorbed within the absorbent pad 12. The absorbent pad 12 does not extend through the lower end of the collapsible tube 16. The internal cross-sectional area of the collapsible tube 16 is larger than the cross-sectional area of the absorbent pad 12 so that the absorbent pad 12 can expand within the collapsible tube 16 when oral fluid has become absorbed within its structure. The collapsible tube 16 is preferably constructed from a material sufficiently durable to allow the donor to chew the end without significant degradation of its structure.

Preferably, a flavouring or odour such as "Juicy Lemon T3602" is incorporated into the collection device 10. The flavouring or odour can be impregnated in the lower end of the collapsible tube 16. Alternatively, the odour may be held in the cap 18 of the collection device 10. The amount of flavouring is controlled so as to not over-stimulate saliva production, which can result in the reduction of drug levels in the oral fluid, producing unreliable results. It is also chosen to not alter the pH of the oral fluid.

The collection device 10 is designed to be of suitable proportions to allow the collapsible tube to be comfortably inserted into the mouth. It must also be large enough to enable the collection of a sufficient volume of oral fluid for testing. In the preferred embodiment the collection device 10 is approximately 70 mm long, with the foam pad 12 measuring 22 mm long, 18 mm wide and 8 mm thick. The collapsible tube 16 is 41 mm long with an external cross-sectional major axis of 24 mm and a minor axis of 13 mm. The chassis 14, collapsible tube 16 and cap 18 are each formed from a suitable plastics material by injection moulding.

A test cartridge 100 containing a test strip 150 is provided to evaluate an oral fluid sample transferred from the collection device 10 for the presence of particular chemical compounds such as drugs. The test cartridge 100 is shown in FIGS. 7 to 12.

Figure 7:
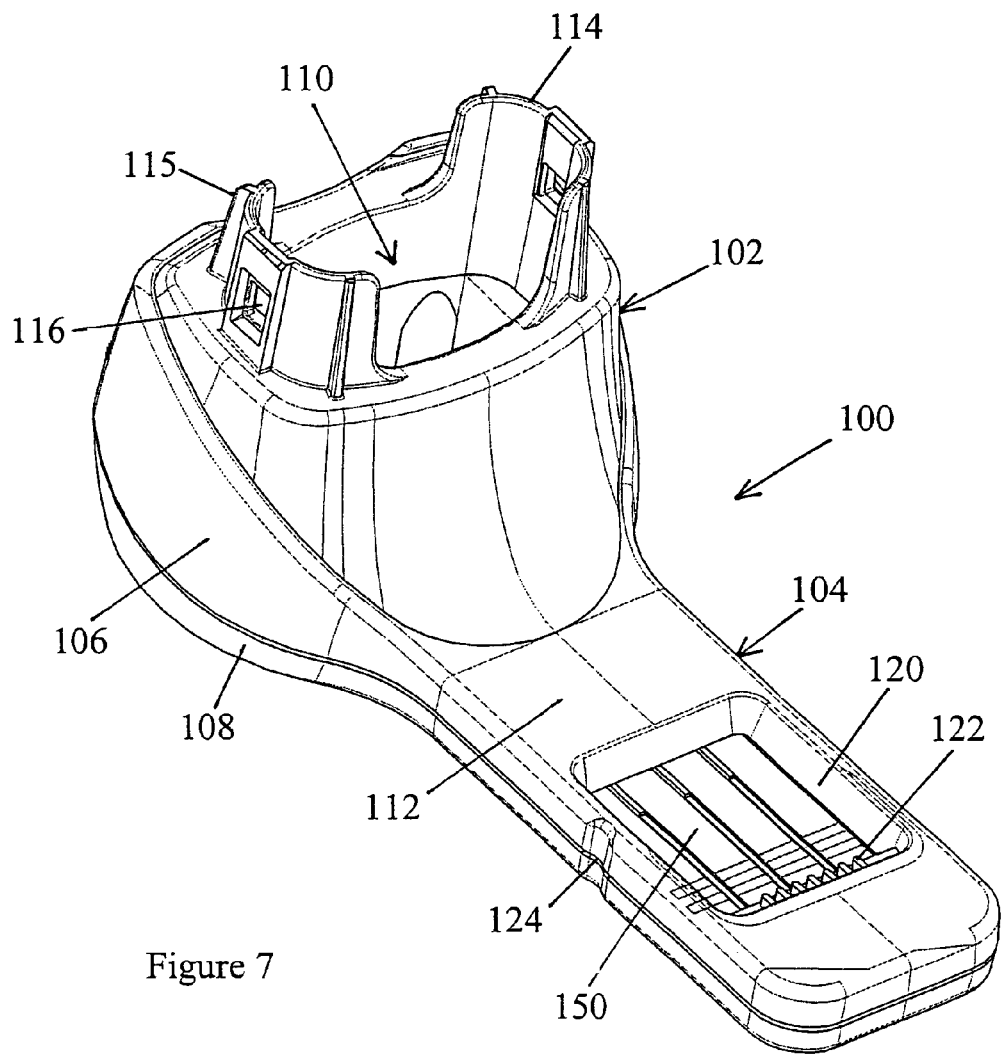
FIG. 7 is an isometric view of a test cartridge for use with the collection device of FIG. 1.
Figure 8:
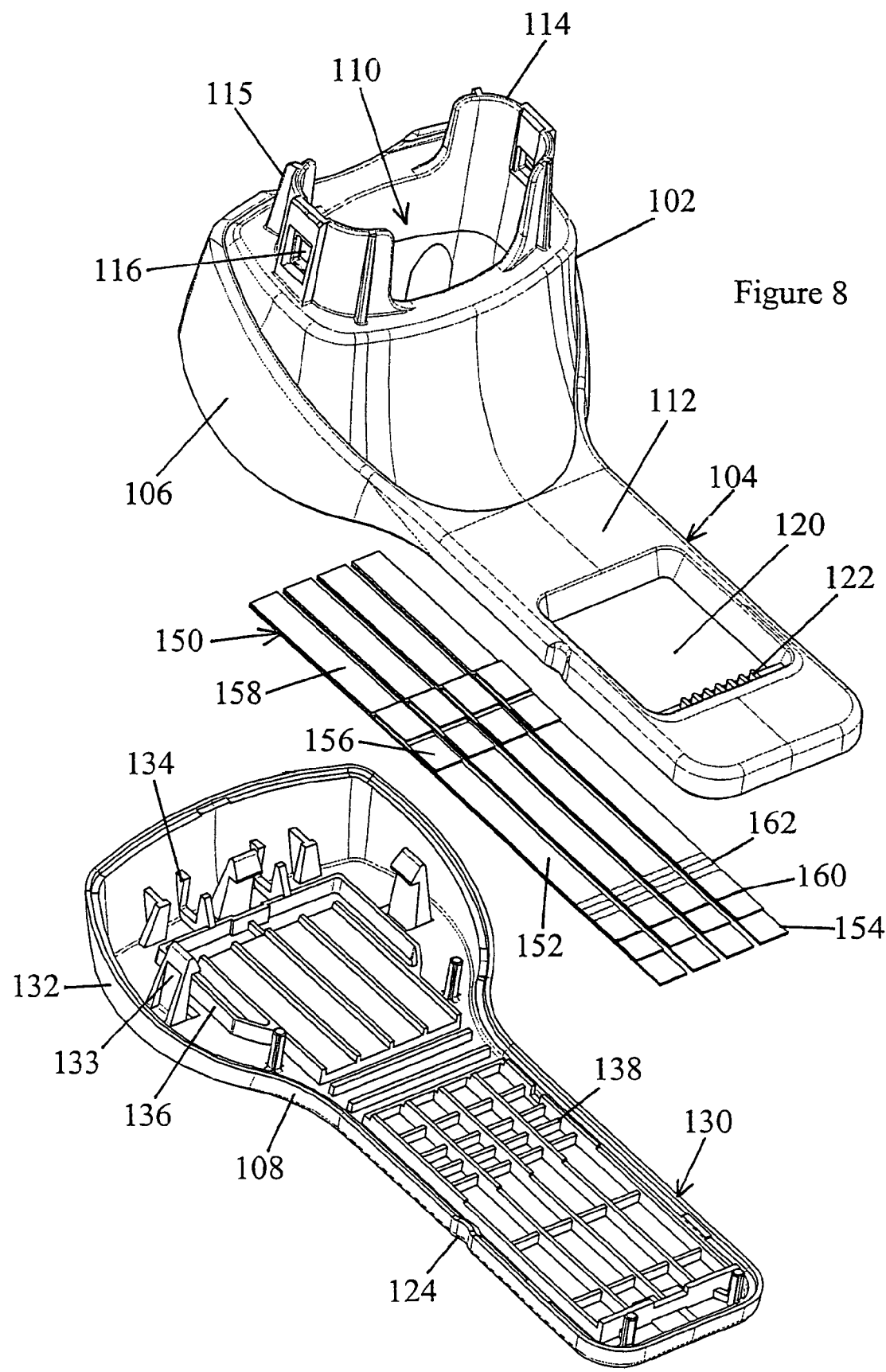
FIG. 8 is an exploded view of the test cartridge of FIG. 7.
Figure 9:
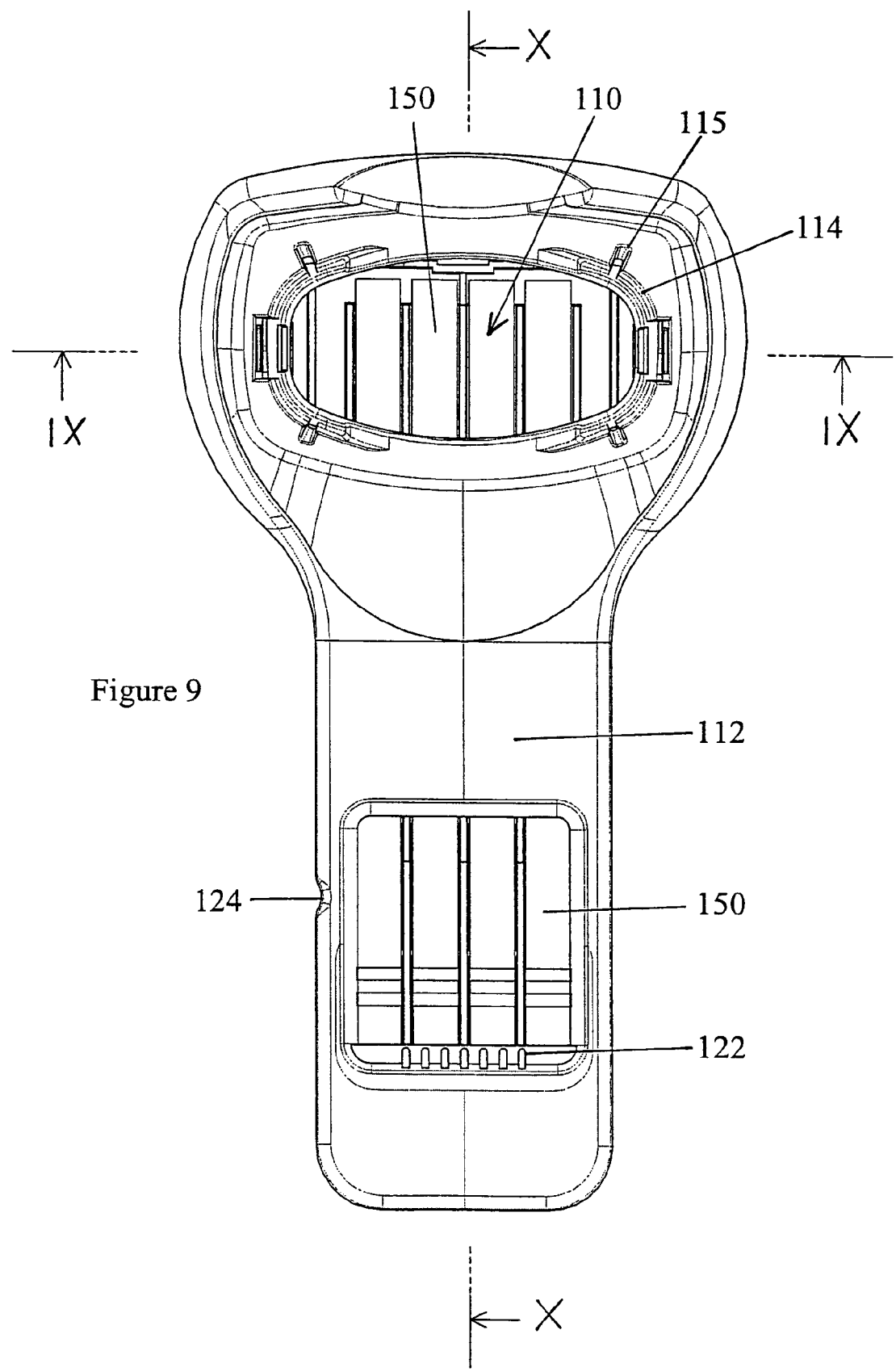
FIG. 9 is a top view of the test cartridge of FIG. 7.

The test cartridge 100 is of generally L-shape with an upstanding portion 102 and a laterally-extending portion 104 which extends from the bottom of the upstanding portion 102. The test cartridge 100 is formed from a top moulding 106 and a base moulding 108. The top moulding 106 has a collection chamber 110 which extends vertically from one end of an elongate rectangular cover section 112 of the top moulding 106. The collection chamber 110 is, as seen in FIGS. 7 and 8, open at both top and bottom, and has an internal cross-section substantially the same size and shape as the external cross section of the collapsible tube 16 of the collection device 10, so that the collapsible tube 16 can be inserted lengthways downwardly into the collection chamber 110. The depth of the collection chamber 110 is shorter than the uncompressed length of the collapsible tube 16 so that the collapsible tube 16 cannot be fully inserted into the collection chamber 110 without becoming at least partially compressed. A pair of upstanding flanges 114 extend upwardly from opposite longitudinal sides of the top rim of the collection chamber 110. Each flange 114 contains a rectangular locking hole 116, positioned to coincide with the corresponding latching portion 48 of the chassis 14 when the collection device 10 is inserted into the collection chamber 110, so that each latching portion 48 can lock into the corresponding locking hole 116. The portion of the interior of the flanges 114 above the locking holes 116 is chamfered so that the latching portions 48 are automatically guided and pushed inward upon inserting the collection device 10 into the collection chamber 110. A series of spines 115 on the exterior of the flanges 114 match with a corresponding series of grooves (not shown) within the cap 18 of the collection device 10 to help guide the collection device 10 into the correct position within the collection chamber 110. The locking holes 116 are located so that the latching portions 48 of the collection device 10 become locked into the locking holes 116 in the flanges 114 only when the collapsible tube 16 and the pad 12 are compressed by a predetermined amount.

The base moulding contains a pair of clips 134, best seen in FIG. 8, which act to hold a desiccant 135, best seen in FIG. 12, to absorb moisture from within the test cartridge 100. A rectangular ridge 136 extends upwardly from the base of the base moulding 108 and partially surrounds the portion of the base moulding 108 which lies directly beneath the collection chamber 110. The ridge 136 prevents the escape of oral fluid from the end of the test strip 150 which lies directly beneath the collection chamber 110 when oral fluid is transferred from the collection device 10 to the test cartridge 100. The laterally extending portion 104 of the test cartridge 100 comprise a number of protrusions 138 which extend downwardly from the cover portion 112 and upwardly from the base portion 130. The protrusions 138 are positioned so that the cover protrusions lie directly above the corresponding base protrusions and are sized so that there is a gap in between the cover protrusions and the base protrusions when the cover 112 is assembled onto the base 130. The protrusions 138 are positioned within the laterally extending portion 104 of the test cartridge 100 where any two components of the test strip 150 are joined so that the test strip 150 passes through the gap in between the base and cover protrusions where two portions of the test strip 150 are joined. The protrusions 138 act to securely hold the various components of the test strip 150 together.

A rectangular window 120 extends transversely across the elongate cover section 112 for a distance less than the overall width of the cover section 112 and extends over a longitudinal length which is less than the overall length of the cover section 112. The window 120 is bounded or all-four sides by the cover section 112 and extends through the entire thickness of the cover section 112 of the top moulding 106. A series of raised markings 122 are impressed onto the edge of the window 120 furthest away from the collection chamber 110. The raised markings 122 uniquely identify the compatibility of the test strip 150 contained within the test cartridge 100 to a particular chemical compound. Additionally, an indentation 124 on the side of the laterally extending portion 104 of the test cartridge 100 provides an identification of the compatibility of the test cartridge 100 and provides a location reference when the test cartridge 100 is inserted into an analyser.

The base moulding 108 of the test cartridge 100 has an elongate rectangular portion 130 with a large bulbous portion 132 at one end. The upper periphery of the base moulding 108 mates with the lower periphery of the top moulding 106. A test strip 150, which may be an immunoassay test strip, is laid onto the upper surface of the base moulding 108 so that the test strip 150 extends longitudinally along the length of the base moulding 108. The large portion 132 of the base moulding 108 fits under the collection chamber 110. The test strip 150 is located such that upon assembly of the test cartridge 100, the test strip 150 is visible through the window 120 of the cover section 112. The test cartridge 100 may contain a single test strip, but it is understood that a plurality of test strips can be contained in the test cartridge 100, with each one testing for a different analyte or multiple analytes. The top moulding 106 is then assembled onto the base moulding 108 by fitting the collection chamber 110 onto the large bulbous portion 132 of the base moulding 108 and the cover section 112 onto the rectangular portion 130 of the base moulding 108. The top and base mouldings 106,108 are joined for example by gluing. Preferably, the top moulding 106 is designed to snap-fit onto the base moulding 108. The base moulding 108 contains a pair of wedge shaped notches 133 on opposite sides of the bulbous portion 132 which match to a corresponding pair of locking holes 140 in the top moulding 106. The notches 133 help to securely fix the top moulding 106 to the base moulding 108 when the force resulting from pushing the collection device 10 into the collection chamber 110 tries to pull them apart. The top moulding 106 is shown as being made of a single unit so that the cover section 112 and the collection chamber 110 are a single piece. However they could be formed by two separate mouldings. The test cartridge 100 is preferably disposable and formed from a suitable plastics material by injection moulding.

The example discussed here relates to testing for drugs of abuse by immunoassay but the invention is applicable to other analytes and to other types of testing.

Figure 13:
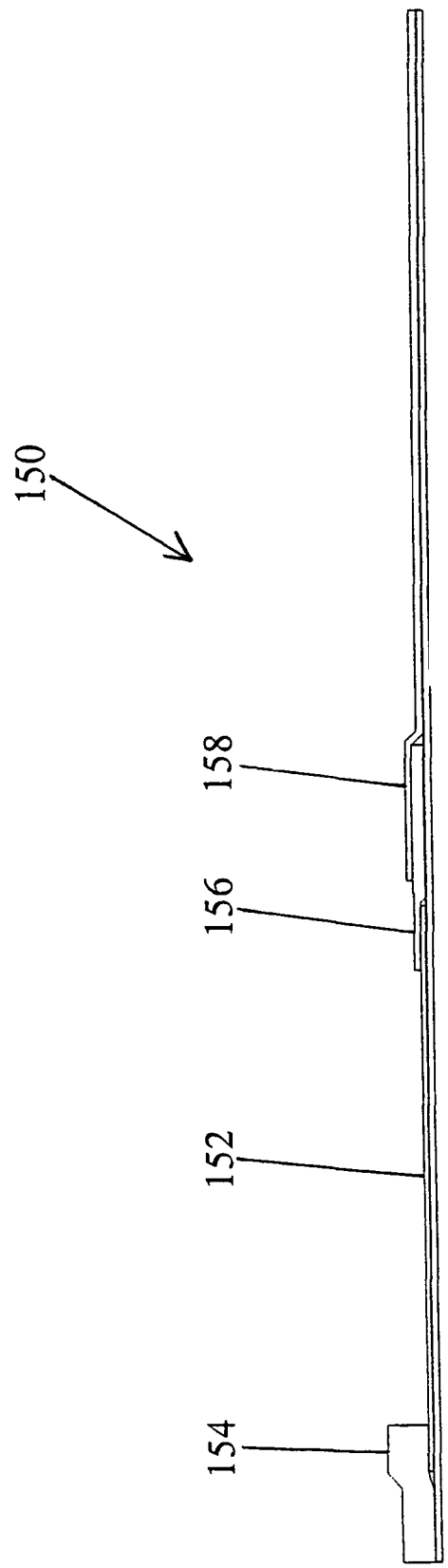
FIG. 13 shows an immunoassay test strip for use in the test cartridge of FIG. 7.

FIG. 13 is a side view of an immunoassay test strip 150. The use of immunoassay strips of this type is known and is described in United States Patent Application 2001/0034068 "Screening device and methods of screening immunoassay tests and agglutination tests" which description will be briefly summarised herein for convenience. For further details, reference should be made to that application.

The upper surface of a flat, elongate nitrocellulose membrane 152 is bonded to a waste pad 154 at one end and to a conjugate release pad 156 at its other end. Both the conjugate release pad 156 and the waste pad 154 overlap the ends of the nitrocellulose membrane 152. The other end of the conjugate release pad 156 is overlapped by an absorbent sample pad 158 and is bonded at its upper surface to the lower surface of the absorbent sample pad 158. When fluid is applied to the sample pad 158 it is drawn along the sample pad 158 by capillary action, through the conjugate release pad 156 and nitrocellulose membrane 152 and surplus fluid is absorbed by the waste pad 154.

The conjugate release pad 156 holds a mobile and visible label, or marker, such as colloidal gold or coloured latex particles (or by other labels such as fluorescent or chemiluminescent label) attached to the revealing agent or ligand such as anti-drug antibody, and is in contact with the nitrocellulose membrane 152 such that when fluid is added to the collection chamber 110, it is drawn by capillary action downstream from the collection chamber 110 through the absorbent sample pad 158, through the conjugate release pad 156, and subsequently through the nitro-cellulose membrane 152. The sample pad may contain additives such as salts and wetting agents that are essential for optimal performance of the test.

At discrete intervals along the nitro-cellulose membrane 152, capture reagents 162 such as drug-protein derivatives or antibody or receptor or protein or enzyme are biochemically bound to the nitro-cellulose membrane 152, producing an immobile zone of reagents such as drug-protein derivative which may span the width of the nitro-cellulose membrane 152, or be in the form of a dot or other pattern. Towards the extreme downstream end of the nitro-cellulose member 152, that is; downstream of all the immobile reagent zones, is a control reagent zone 160 which also spans the width of the nitro-cellulose membrane 152. Multiple zones 162 may be used on each test strip to allow testing of more than one analyte on each strip. The zones are separated by background zones (not shown) where the nitrocellulose membrane 152 does not have bound capture reagents such as drug conjugate. In the example of drug testing, antibodies to each drug which is to be tested for, conjugated with colloidal gold, are placed on the conjugate release pad 156 for the respective strip or zone. When oral fluid is transferred from the collection device 10 onto the sample pad 158, the resulting sample passes across the absorbent sample pad 158 and across the conjugate release pad 156 where it hydrates and mixes with the revealing reagents (for example, antibody-gold conjugates). The sample and revealing agent then travel the length of the nitrocellulose membrane 152.

If the particular drug is present in the sample it will bind to the antibody-gold conjugate. When the sample and reagent mixture subsequently passes over the specific drug-protein derivative, the antibody-gold conjugate has already been bound to the drug in the sample and is not free to bind with the drug-protein derivative bonded to the membrane. If the particular drug is absent from the sample, the antibody-gold conjugate will be free to bind to the drug-protein conjugate causing the antibody-gold conjugate to become immobilised at the site of the drug-protein conjugate. The visible marker is deposited in the test zone as a coloured line or stripe. In between these two extremes some of the antibody-gold conjugate will bind with the drug-protein derivatives on the strip creating an intermediate intensity of colour. The intensity of the colour on the particular drug-protein zone is therefore inversely proportional to the amount of drug present in the sample.

The depth of colour of the control zone should always be significant and the control zone 160 is designed with this in mind. The colour of the control zone can then be used to indicate that the test has been successfully run and could be used to provide threshold or comparison for the colour levels in specific drug conjugate zones.

Figure 14:
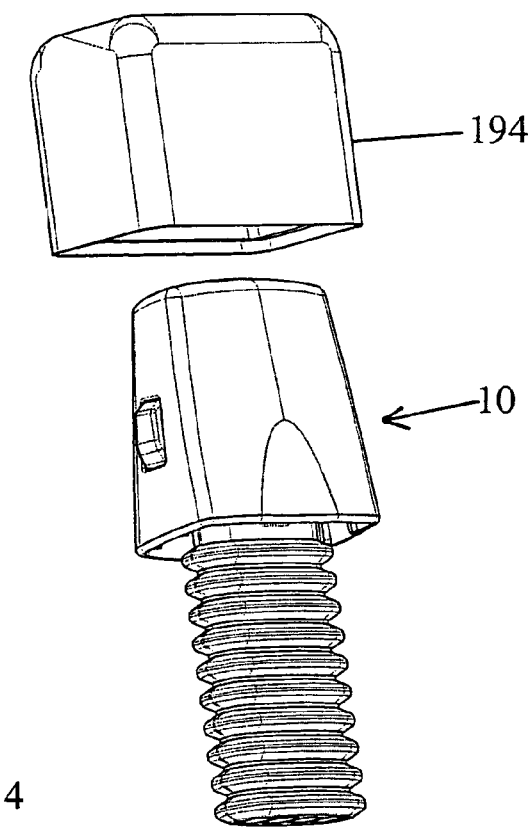
FIG. 14 is an exploded view of a transportation vial with the collection device of FIG. 1.
Figure 14:
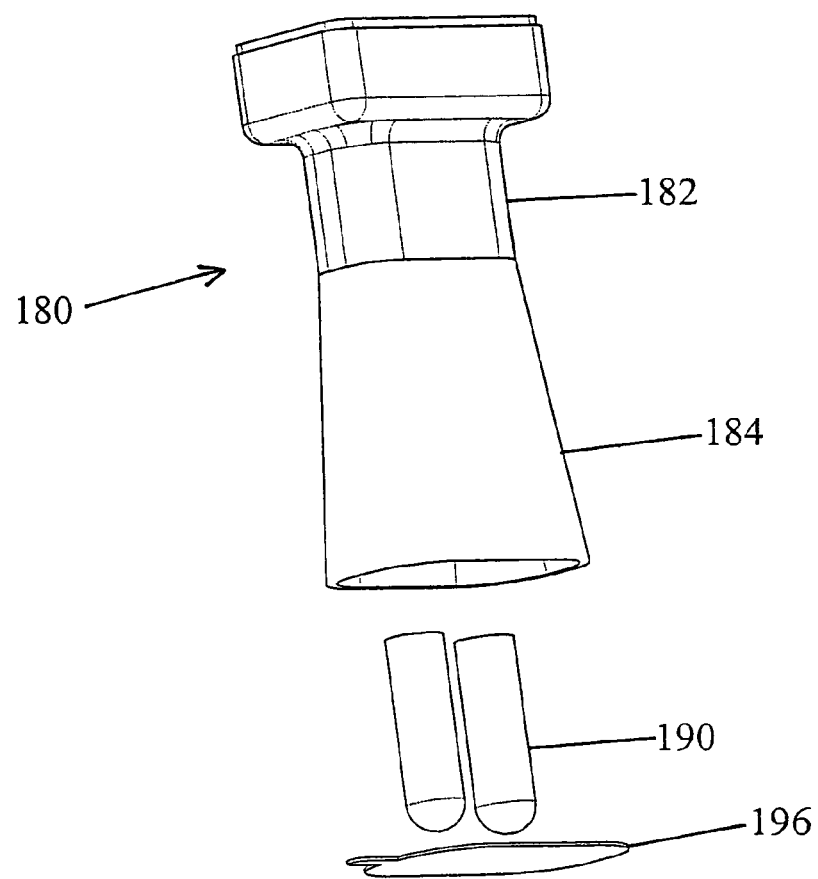
Figure 15:
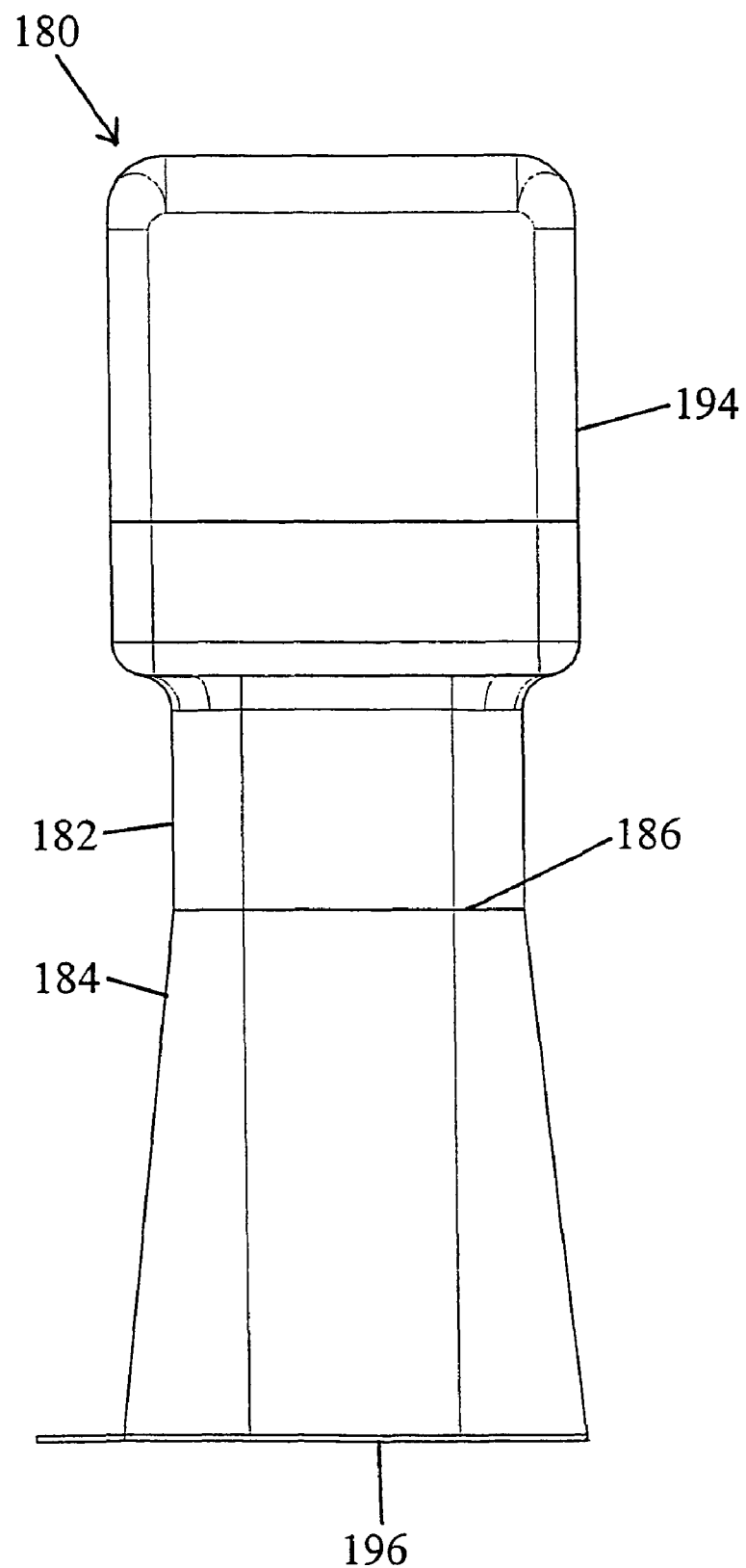
FIG. 15 is an assembled front view of the transportation vial of FIG. 14.
Figure 16:
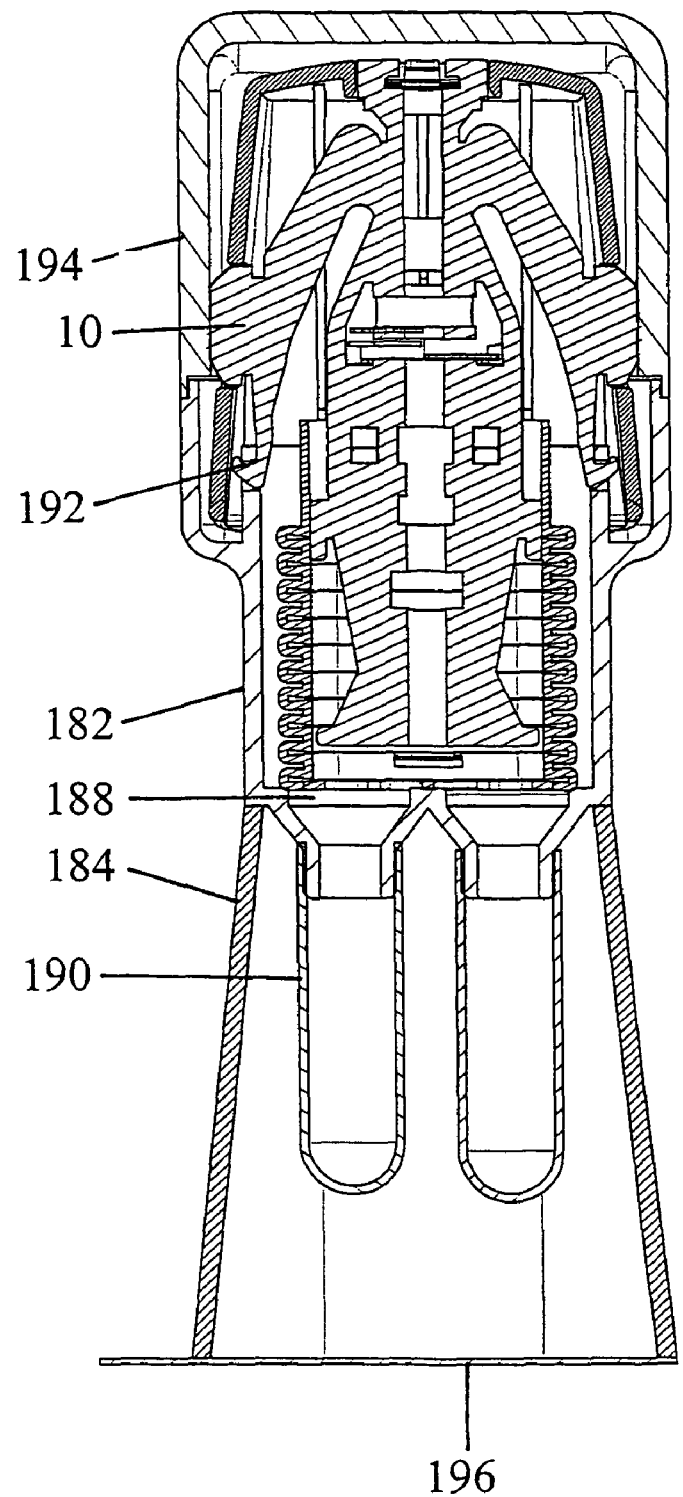
FIG. 16 is a front cross-section of the transportation vial of FIG. 15.

FIG. 14 is an exploded view of a transportation vial with the collection device of FIG. 1. FIG. 15 is an assembled front view of the transportation vial of FIG. 14. FIG. 16 is a front cross-section of the transportation vial of FIG. 15. The transportation vial 180 consists of an open-ended container comprising a neck portion 182 whose walls are substantially vertical, and a body portion 184. The internal cross section of the neck 182 is substantially the same size and shape as the external cross section of the collapsible tube 16 so that the collapsible tube 16 can be inserted lengthways into the neck 182 of the transportation vial 180. Part way up the interior of the transportation vial 180 is a horizontal shelf 186 which extends across the entire cross section of the transportation vial 180 and which separates the internal volume of the transportation vial 180 into two portions. The shelf 186 is positioned a distance below the opening of the transportation vial 180 which is shorter than the uncompressed length of the collapsible tube 16 so that the collapsible tube 16 cannot be inserted fully into the transportation vial 180 without becoming at least partially compressed. The shelf 186 contains at least one small opening 188 so that oral fluid can pass through the shelf 186 from the neck portion 182 into the body portion 184.

In the preferred embodiment the body portion 184 contains at least one small collection or sample vial 190. The opening of each sample vial 190 is positioned directly beneath, and is at least as large as a respective one of the small openings 188 in the shelf 186 so that all of the oral fluid which passes through the openings 188 in the shelf 186 is collected within the sample vial 190. Each sample vial 190 preferably contains a preservative such as an anti-microbial agent to prevent degradation of the oral fluid sample by native bacteria during transportation of the sample to a laboratory. A pair of locking holes 192 are positioned on opposite sides of the interior of the neck 182 of the transportation vial 180. The locking holes 192 are positioned to coincide with the latching portion 48 of the locking mechanism when the collection device 10 is inserted into the transportation vial 180 so that the latching portions 48 lock into the locking holes 192. The locking holes 192 are located so that the latching portion 48 of the collection device 10 become locked into the locking holes 192 in the transportation vial 180 only when the collapsible tube 16 and the absorbent pad 12 are compressed by a predetermined amount in the same manner as with the test cartridge 100.

The transportation vial 180 further comprises a lid 194 which can be fitted to the open top of the transportation vial 180. The lid 194 is large enough so that it can be fitted even when the collection device 10 remains located inside the transportation vial 180. The lid 194 can be snap fitted to the transportation vial 180 or alternatively, a catch could be used. In the preferred embodiment, the lid 194 is further sealed with a tamper proof seal (not shown) to prevent the oral fluid sample being compromised during transportation. The bottom of the transportation vial 180 consists of a membrane 196 which can be removed by for example peeling away. This allows for access to the sample vials 190 contained within the body portion 184 of the transportation vial 180. The transportation vial 180 can be made of any suitable plastics material by for example blow moulding. The sample vials 190 can be made from either a suitable plastics material or glass. In the preferred embodiment, the transportation vial 180 is 113 mm tall with the lid, 40 mm long and 26 mm wide. The shelf 186 is positioned so that the neck portion 182 of the transportation vial is 34 mm deep.

The operation of the system illustrated will now be described. A collection device 10 is provided to enable the collection and transfer of a precise predetermined volume of oral fluid. In the preferred embodiment, the system allows the transfer of a predetermined volume of oral fluid to the test cartridge 100 within an error of approximately 10%. The donor holds the collection device 10 by the protective cap 18 and inserts the open end of the collapsible tube 16 into the mouth. If the oral fluid production rate of the donor is too low to enable an adequate volume of oral fluid to be collected in a convenient time, the donor can chew the end of the collapsible tube 16. This action causes a physiological response of stimulating the saliva glands of the donor thereby increasing the oral fluid production rate. The saliva glands of the donor can be further stimulated by the presence of a flavouring or odour incorporated into the collection device 10. In the preferred embodiment, an adequate volume of oral fluid is normally collected within a few minutes. Oral fluid passes from the mouth through the openings 68 in the end of the collapsible tube 16 and into the interior of the collapsible tube 16 where it is drawn into the absorbent pad 12 by absorbency. As oral fluid is absorbed into the absorbent pad 12, the absorbent pad 12 expands to hold the fluid within its structure. If the system described herein is being used to collect and test fluid other than oral fluid, the collection device 10 can be inserted into a source of fluid to be tested.

As more oral fluid is absorbed into the absorbent pad 12, the oral fluid is drawn upwards through the absorbent pad 12 towards the upper surface of the absorbent pad 12 where the fluid sensitive contact 64 is located. When a sufficient volume of oral fluid has been absorbed by the absorbent pad 12, the upper surface of the absorbent pad 12 where the fluid sensitive contact 64 is located will be hydrated. The presence of oral fluid surrounding the fluid sensitive contact 64 causes the two series of conducting elements to become electrically connected and thus the fluid sensitive contact 64 to become bridged. The electrical circuit of the fluid adequacy indicator 20 will thus be completed and current will flow from the battery 62 through the bridged fluid sensitive contact 64 to the LED 66 causing the LED 66 to light. The user sees the activation of the LED 66 which signal informs the operator that an adequate volume of oral fluid has been collected.

Next, oral fluid is transferred from the collection device 10 to the test cartridge 100. FIG. 10 is an isometric view of the collection device 10 fully inserted into the test cartridge 100. FIG. 11 is a front cross-section of the collection device 10 fully inserted into the test cartridge 100. FIG. 12 is a side cross-section of the collection device 10 fully inserted into the test cartridge 100. The collapsible tube 16 is inserted into the collection chamber 110 of the test cartridge 100 and the collection device 10 is pushed downwardly until the latching portions 48 of the arms 44 of the chassis 14 become locked into the locking holes 116 in the collection chamber 110. The depth of the collection chamber 110 is shorter than the unextended length of the collapsible tube 16 so that the latches 48 cannot become locked into the locking holes 116 without at least partially compressing the collapsible tube 16. When the collapsible tube 16 becomes compressed, the plunger structure 34 of the chassis 14 exerts a downwards force on the absorbent pad 12 and causes the absorbent pad 12 to become compressed. As the user applies a downwards force to the collection device 10, the chassis 14 will tend to move upwards inside the cap 18. The shelf 55 on the top portion 54 of the chassis 14 engages the interior of the roof of the cap 18 of the collection device 10 and prevents the chassis 14 from moving upwards inside the cap 18. As the absorbent pad 12 becomes compressed, an excess of oral fluid which had previously been absorbed in the absorbent pad 12 is squeezed out. The excess fluid runs downwards onto the sample pad 158 of the test strip 150 which lies at the base of the collection chamber 110. The configuration of the locking mechanism formed by the latching portions 48 and locking holes 116 is such that the latches 48 become locked into the locking holes 116 only when the absorbent pad 12 and collapsible tube 16 have been compressed by predetermined and controlled amount. The locking mechanism provides a means to indicate to the operator when the absorbent pad 12 has been compressed by a sufficient amount and prevents excessive compression of the absorbent pad 12. This controlled degree of compression results in a predetermined volume of the oral fluid absorbed in the absorbent pad 12 becoming transferred to the test strip 150. In one embodiment, the compression of the absorbent pad 12 is such that after the compression of the absorbent pad 12, some oral fluid remains absorbed in the absorbent pad 12.

The oral fluid applied to the sample pad 158 is drawn along the sample pad 158 by capillary action, through the conjugate release pad 156 and nitrocellulose membrane 152, and surplus fluid is absorbed by the waste pad 154. The visible marker is deposited onto the test zone where it is displayed through the window 120. The laterally extending portion 104 of the test cartridge 100 is inserted into an analyser suitable for analysing the test strip 150 and displays the results of the test. The analyser accesses the test zone of the test strip 150 by interfacing with the window 120. Such an analyser is described in the aforementioned United States Patent Application 2001/0034068. The analyser first analyses the raised markings 122 at the edge of the window 120 to verify that the test cartridge 100 contains a compatible test strip. The analyser additionally analyses the indentation 124 on the side of the laterally extending portion 104 to ensure that the test cartridge 100 is inserted in the correct position within the analyser. Alternatively, the test could be analysed visually by the operator. The collection device 10 is released from the test cartridge 100 when the test has completed by pushing inwardly each of the release buttons 46. The collection device 10 is pushed down a small distance to allow the ridges 49 at the tips of the latches 48 to become freed from the locking holes 116. The flexible arms 44 flex inwardly and the latches 48 become released from the locking holes 116 allowing the collection device 10 to be lifted from the collection chamber 110.

Oral fluid is then transferred from the collection device 10 into the transportation vial 180. The collapsible tube 16 is inserted into the neck portion 182 of the transportation vial 180 and pushed down until the latching portion 48 of the locking mechanism become locked into the locking holes 192 in the neck 182 of the transportation vial 180. The shelf 186 prevents the collapsible tube 16 being fully inserted into the transportation vial 180 without becoming at least partially compressed. The plunger structure 34 of the chassis 14 exerts a downwards force on the absorbent pad 12 which causes the absorbent pad 12 to become compressed. The compression of the absorbent pad 12 causes an excess of oral fluid to be squeezed out of the absorbent pad 12 which runs down through the openings 188 in the shelf 186 and into the collection vials 190. Preferably, the shelf 186 is positioned so that the compression of the absorbent pad 12 causes the remaining oral fluid absorbed within the absorbent pad 12 to be expelled. The collection device 10 is released from the transportation vial 180 by pushing each release button 46 inwardly. The lid 194 of the transportation vial 180 is fitted sealing the sample of oral fluid with the preservative within the sample vial 190.

The collection device 10 and transportation vial 180 are then sent to a laboratory for confirmation or further testing preferably within secure packaging sealed with a tamper evident seal. The sample of oral fluid contained within the sample vial 190 provides the laboratory with a working sample to test. The laboratory technicians are able to access the oral fluid samples within the sample vials by removing the membrane 196 at the bottom of the transportation vial 180 and removing the sample vials 190.

Thus as seen from the foregoing the system comprises an oral fluid collection and transfer device with a collection device 10 and a test cartridge 100. The system additionally comprises an oral fluid transportation device 180. The collection device includes a frame or chassis 14, and an absorbing pad 12 for absorbing oral fluid and which is secured around part of the frame 14 with part of the frame 14 protruding from the pad 12. A collapsible cover 16 covers the absorbing pad 12 and has apertures 68 for the ingress of oral fluid into contact with the absorbing pad 12. A cap 18 covers the part of the frame 14 protruding from the absorbing pad 12. The cap 18 and the cover 16 latch together to surround the frame 14 and the absorbing pad 12. The device also includes a fluid adequacy indicator 20 in the form of an electrical circuit with an LED 66 which is completed when the absorbing pad 12 has absorbed a predetermined volume of oral fluid. The test cartridge 100 has a collection chamber 110 to allow insertion of the collection device 10 into the test cartridge 100. A test strip 150 is used to test the oral fluid for the presence of analytes. The collection device 10 is located at a fixed location relative to the test cartridge 100 within the collection chamber 110, in which location the absorbing pad 12 undergoes a controlled degree of compression, thereby transferring a predetermined volume of oral fluid from the absorbing pad 12 to the test strip 150.

Figure 17:
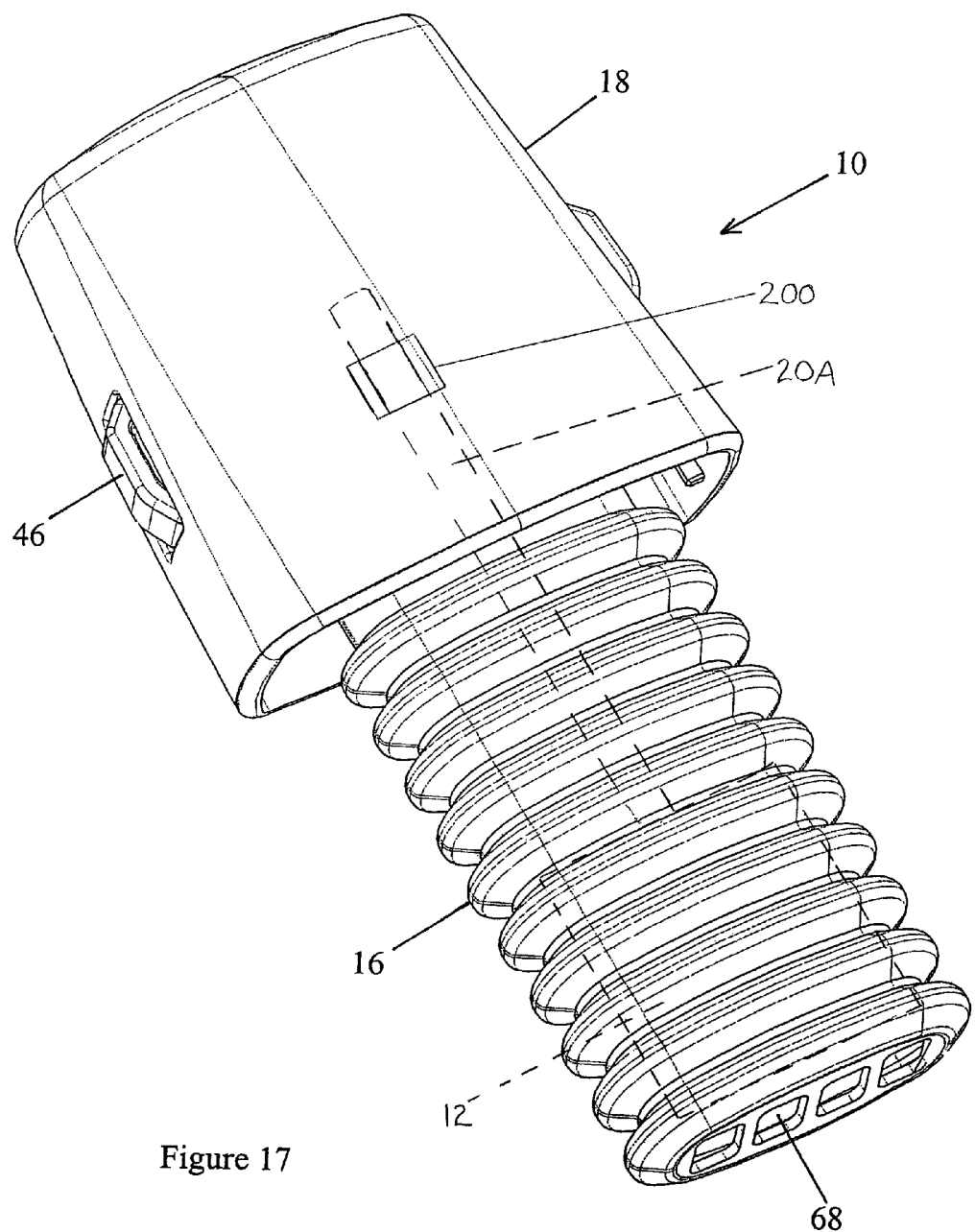
FIG. 17 shows a second embodiment of an assembled collection device with a chemical based fluid adequacy indicator.

In another embodiment shown in FIG. 17, a chemical based fluid adequacy indicator is used. In this embodiment, the absorbent pad 12 contains a Porex®, glass fiber or cellulose wick 20A. As oral fluid travels up the wick 20A, a fluid sensitive chemical dye is re-hydrated causing a change in colour of the dye which is displayed to the operator through a window 200 in the collection device. Alternatively, a coloured dye travels with the oral fluid until visible in a window.

The system described herein above provides a number of advantages with respect to the collection and testing of oral fluid. The apparatus is portable and convenient to use. The incorporation of a fluid adequacy indicator removes subjective judgement from the oral fluid collection process. The collection device further incorporates means to stimulate the donor's saliva glands to provide apparatus for the collection of oral fluid in a short time. The apparatus provides for the consistent and accurate testing of oral fluid by providing an error free system of transfer of oral fluid to a test cartridge. The use of a separate collection device and testing device provides the advantage that the donor does not have to place into his mouth a device which may contain toxic or unpleasant chemical compounds used for testing. The use of a transportation vial provides a means to securely verify an oral fluid test at a laboratory, thereby increasing the reliability of the test.

With respect to the above description, it is to be realised that equivalent apparatus and methods are deemed readily apparent to those skilled in the art, and all equivalent apparatus and methods to those illustrated in the drawings and described in the specification are intended to be encompassed by the present invention. It should be noted that the features described by reference to particular figures and at different points of the description may be used in combinations other than those particularly described or shown. For example, it is understood that the collection device and the transportation vial could be used together without making use of the test cartridge. Therefore, the foregoing is considered to be illustrative only of the principles of the invention.

Further, since numerous modifications and changes will readily occur to those skilled in the art, it is not desired to limit the invention to the exact construction and operation shown and described, and accordingly, all suitable modifications and equivalents may be resorted to, falling within scope of the invention. For example, it is readily apparent to those skilled in the art that the present invention is not limited only to the testing of oral fluid in humans, but to the testing of other human or animal biological fluid, or other fluids such as water.

The invention claimed is:

1. Apparatus for the collection and testing of oral, or other fluids, comprising a collection device and a test cartridge wherein:
   the collection device comprises
   (a) absorbing means for absorbing fluid,
   (b) a collapsible cover within which the absorbing means is housed, and
   (c) a fluid adequacy indicator in fluid communication with said absorbing means to receive said fluid absorbed by said absorbing means which said indicator detects the fluid absorbed by said absorbing means disposed in said collapsible cover for signaling when the absorbing means has absorbed a predetermined volume of fluid; and
   the test cartridge comprises
   (a) a collection chamber which allows insertion of the collection device into the test cartridge,
   (b) a test strip in fluid communication with said collection chamber for testing fluid for the presence of analytes, and
   (c) a locating structure which locates the collection device at a fixed location relative to the test cartridge within the collection chamber, in which location said collapsible cover is held in a compressed state by said locating structure such that the absorbing means has undergone a controlled degree of compression which transfers a predetermined volume of fluid from the absorbing means to the test strip.

2. Apparatus according to claim 1, wherein the collection device further comprises a plunger located above the absorbing means such that when the collection device is inserted into the test cartridge, the plunger applies a force to the absorbing means thereby at least partially compressing the absorbing means.

3. Apparatus according to claim 1, wherein the depth of the collection chamber is shorter than the uncompressed length of the collapsible cover such that the absorbing means cannot be fully inserted into the collection chamber without being at least partially compressed.

4. Apparatus according to claim 2, wherein the locating structure comprises a locking mechanism which defines the controlled degree of compression by said plunger, wherein said locking mechanism locates the collection device inside the test cartridge in a relative position such that the locking mechanism is activated only when the absorbing means is compressed by a predetermined amount by said plunger.

5. Apparatus according to claim 4, wherein the locking mechanism comprises:
   a pair of flexible arms wherein the collection device comprises said flexible arms and an outwardly facing latch is positioned at the end of each of the flexible arms; and
   a pair of corresponding locking holes situated in the test cartridge which correspond to the outwardly facing latches;
   and wherein upon insertion of the collection device into the test cartridge, each of the latches is configured to engage a corresponding one of the locking holes when the absorbing means has been compressed by a predetermined amount to hold said collapsible cover in said compressed state.

6. Apparatus according to claim 5, wherein the locking mechanism is releasable.

7. Apparatus according to claim 1, wherein the absorbing means comprises a pad made of a cellulose or foam material.

8. Apparatus according to claim 1, wherein the absorbing means absorbs at least 0.6 ml of fluid.

9. Apparatus according to claim 1, wherein the collapsible cover is a deformable material which is durable and flexible to sustain chewing for collection of said fluid while said collapsible cover maintains an uncompressed state when not being chewed.

10. Apparatus according to claim 1, wherein the collapsible cover includes an odor or flavoring.

11. Apparatus according to claim 1, wherein the fluid adequacy indicator comprises an electronic circuit including a power source, a fluid sensitive contact and an alerting device.

12. Apparatus according to claim 11, wherein the alerting device is a buzzer.

13. Apparatus according to claim 11, wherein the alerting device is a light emitting device.

14. Apparatus according to claim 11, wherein the electronic circuit further comprises a timing device.

15. Apparatus according to claim 1, wherein the fluid adequacy indicator comprises a chemical based indicator.

16. Apparatus according to claim 15, wherein the fluid adequacy indicator comprises a wick comprising one of Porex™, glass fibre and cellulose in which a fluid sensitive chemical dye is able to be hydrated by said fluid.

17. Apparatus according to claim 1, wherein the test cartridge further comprises markings which uniquely identifies the compatibility of the test strip.

18. Apparatus according to claim 1, wherein the test cartridge comprises a plurality of test strips, and wherein fluid is transferred from the collection device to each of the plurality of test strips.

19. Apparatus according to claim 18, wherein each of the plurality of test strips is able to test for a different analyte or multiple analytes.

20. Apparatus according to claim 1,
   further comprising a transportation vial engagable with said collection device for transportation of a sample of fluid to a laboratory, wherein the transportation vial contains at least one sample vial for collection of fluid from said collection device, and comprises a neck portion which reclines said collapsible cover for insertion of the collection device into the transportation vial and means for locating the collection device at a fixed location relative to the transportation vial within the neck portion, in which location the absorbing means undergoes a controlled degree of compression thereby transferring a predetermined volume of fluid from the absorbing means to the at least one sample vial.

21. Apparatus according to claim 1, wherein:

the collapsible cover has apertures for the ingress of fluids, and the collection device further comprising:

a frame, having a first part contained within the collapsible cover and forming a compressor structure to compress the absorbing means, and a second part which protrudes from the upper end of the collapsible cover;

a cap for covering the second part of the frame protruding from the collapsible cover; and engaging means for attaching the cap and the cover to surround the frame;

wherein compression of the collapsible cover causes the compressor structure to compress the absorbing means to force fluid absorbed by the absorbing means out of the absorbing means.

22. Apparatus according to claim 21, further comprising a transportation vial engagable with said collection device for transportation of a sample of fluid to a laboratory, wherein the transportation vial contains at least one sample vial for collection of fluid from said collection device, and comprises a neck portion which receives said collapsible cover for insertion of the collection device into the transportation vial and means for locating the collection device at a fixed location relative to the transportation vial within the neck portion, in which location the absorbing means undergoes a controlled degree of compression thereby transferring a predetermined volume of fluid from the absorbing means to the at least one sample vial.

23. Apparatus for the collection and testing of oral, or other fluids, comprising a collection device and a test cartridge which are selectively engagable together wherein:

the collection device comprises (a) absorbing means for absorbing fluid, (b) a collapsible cover within which the absorbing means is housed and enclosed, and (c) a fluid adequacy indicator in fluid communication with said absorbing means to receive said fluid absorbed by said absorbing means, which said fluid adequacy indicator detects the absorbed fluid absorbed by said absorbing means disposed in said collapsible cover and signals externally of said collection device when the absorbing means has absorbed a predetermined volume of said absorbed fluid; and the test cartridge comprises (a) a collection chamber to allow insertion of the collection device into the test cartridge, (b) a test strip wherein said test cartridge has said test strip positioned in fluid communication with said collection chamber for receiving said absorbed fluid from said collection device, and for testing said absorbed fluid for the presence of analytes; and (c) a locating structure which locates the collection device at a fixed location relative to the test cartridge within the collection chamber, in which location said collapsible cover is held in a compressed state by said locating structure, in which said compressed state the absorbing means has undergone a controlled degree of compression to a compressed volume, which said compressed volume of said absorbing means expels a predetermined volume of said fluid from the absorbing means to the test strip.

\* \* \* \* \*